(12) United States Patent
Brown

(10) Patent No.: US 9,603,369 B2
(45) Date of Patent: Mar. 28, 2017

(54) CLONOSTACHYS ROSEA INOCULATED PLANT MATERIALS WITH FUNGICIDES AND ADJUVANTS

(71) Applicant: Adjuvants Plus USA, INC., Lansing, MI (US)

(72) Inventor: William Gordon Brown, Kingsville (CA)

(73) Assignee: Adjuvants Plus USA, Inc., Lansing, MI (US)

( * ) Notice: Subject to any disclaimer, the term of this patent is extended or adjusted under 35 U.S.C. 154(b) by 0 days.

(21) Appl. No.: 14/799,349

(22) Filed: Jul. 14, 2015

(65) Prior Publication Data

US 2016/0007613 A1    Jan. 14, 2016

Related U.S. Application Data

(60) Provisional application No. 62/024,137, filed on Jul. 14, 2014.

(51) Int. Cl.
| | | |
|---|---|---|
| *A01N 25/00* | (2006.01) | |
| *A01N 63/00* | (2006.01) | |
| *A01N 63/02* | (2006.01) | |
| *A01N 63/04* | (2006.01) | |

(52) U.S. Cl.
 CPC ................... *A01N 63/04* (2013.01)

(58) Field of Classification Search
None
See application file for complete search history.

(56) References Cited

U.S. PATENT DOCUMENTS

| | | | |
|---|---|---|---|
| 4,245,432 A | 1/1981 | Dannelly | |
| 4,272,417 A | 6/1981 | Barke et al. | |
| 4,808,430 A | 2/1989 | Kouno et al. | |
| 5,876,739 A | 3/1999 | Turnblad et al. | |
| 6,495,133 B1 | 12/2002 | Xue | |
| 8,288,315 B2 * | 10/2012 | Voeste | A01N 47/38 504/100 |
| 2002/0115565 A1 | 8/2002 | Asrar et al. | |
| 2003/0176428 A1 | 9/2003 | Schneidersmann et al. | |
| 2008/0004178 A1 | 1/2008 | Ding et al. | |
| 2012/0021906 A1 | 1/2012 | Sutton et al. | |
| 2014/0039018 A1* | 2/2014 | Tateishi | A01N 43/653 514/383 |
| 2014/0148338 A1 | 5/2014 | Hoffmann et al. | |
| 2014/0148411 A1 | 5/2014 | Bartels et al. | |
| 2014/0171474 A1 | 6/2014 | Desbordes et al. | |

FOREIGN PATENT DOCUMENTS

| | | | |
|---|---|---|---|
| CA | WO 00/18241 | | 4/2000 |
| WO | WO 2008132021 | * | 11/2008 |
| WO | WO 2010/108267 A1 | | 9/2010 |
| WO | WO 2013/188366 A2 | | 12/2013 |
| WO | WO2013188366 A2 | | 12/2013 |

OTHER PUBLICATIONS

International Search Report and the Written Opinion of the International Searching Authority, for PCT Application No. PCT/US2015/040418, Issued Sep. 15, 2015.
Cota, LV et al: "Biological Control by *Clonostachys rosea* as a key component in the integrated management of strawberry gray mold", Biological Control, San Diego, CA US vol. 50, No. 3, Sep. 1, 2009, pp. 222-230.
K.W. Reeh at al: "Laboratory Efficacy and fungicide compatibility of *Clonostachys rosea* against Botrytis blight on lowbush blueberry", Candian Journal of Plant Science, vol. 93, No. 4, Jul. 1, 2013, pp. 639-642.
Paulo E.F. Macedo et al.: "Sensitivity of four isolates of *Clonostachys rosea* to pesticides used in the strawberry crop in Brazil," Journal of Pesticide Science, vol. 37, No. 4, Jan. 1, 2012, pp. 333-337.
Zhang, et al., Investigation on the mechanism of of the fungus *Clonostachys rosea* against nematodes using the green fluorescent protein, Applied Microbiol Biotechnol (Published Feb. 22, 2008) 78:983-990.
Xue, et al., Biological control of fusarium head blight of wheat with *Clonostachys rosea* strain ACM941, Can. J. Plant Pathol., vol. 31, 2009.
Reeh, et al., Laboratory efficacy and fungicide compatibility of *Clonostachys rosea* against Botrytis blight on lowbush blueberry, Can. J. Plant Science, 639-642, Jul. 2013, 93(4), Abstract.
Rao, et al., Bio-priming of seeds: A potential tool in the integrated management of alternaria blight of sunflower, Helia, 32 Nr. 50, pp. 107-114 (2009).
Macedo, et al., Sensitivity of four isolates of *Clonostachys rosea* to pesticides used in the strawberry crop in Brazil, J. Pestic. Sci. 37(4), 333-337 (2012).
Kakeya, et al., Biotransformation of the Mycotoxin, Zearalenone, to a Non-estrogenic Compound by a Fungal Strain of *Clonostachys* sp., Biosci., Biotechnol. Biochem., 66(12), 2723-2726 (2002).
Dubey, et al., Hydrophobins are required for conidial hydrophobicity and plant root colonization in the fungal biocontrol agent *Clonostachys rosea*, BMC Microbiology 14:18 http:www.biomedcentral.com/1471-2180/14/18 (2014).
Callan, et al., Bio-priming Treatment for Biological Control of Pythium ultimum Preemergence damping-off in sh2 Sweet Corn, Plant Dis. 74:368-372, The American Phytopathological Society, Plant Disease/vol. 74, No. 5 (1990).
Adjuvants Plus, A Nanotechnology Delivery System for EndoFine, Press Release, Jan. 18, 2013.

* cited by examiner

*Primary Examiner* — Alton Pryor
(74) *Attorney, Agent, or Firm* — O'Kelly & Ernst, LLC; Thomas H. Kramer

(57) ABSTRACT

*Clonostachys rosea* strains have novel usefulness as inoculants of plants promoting plant vigor, health, growth, yield and a reduction of competitive stress caused by other fungi when used alone or sequentially with many fungicides in an integrated pest management system (IPM). Seed and foliar uses are shown to inoculate and subsequently achieve endophytic colonization of the portion of the plant treated. While the germinating conidia of this organism has been shown to tolerate several fungicide groups, the established mycelium of *Clonostachys rosea* is significantly more tolerant to systemic fungicides facilitating use in seed and foliar applications. Seed treatment and colonization may occur at any time after harvest resulting in endophyte enhanced seed that ignores or is marginally altered by other fungal organisms and may be suitable for Feed, Food and Seed uses.

6 Claims, 14 Drawing Sheets

SD water — Acapela — Folicur
Prosaro — Caramba — Headline — Tilt 4 days      8 days Greater root development and less shoot development indicating rapid uptake when Cwet is added to C. rosea.

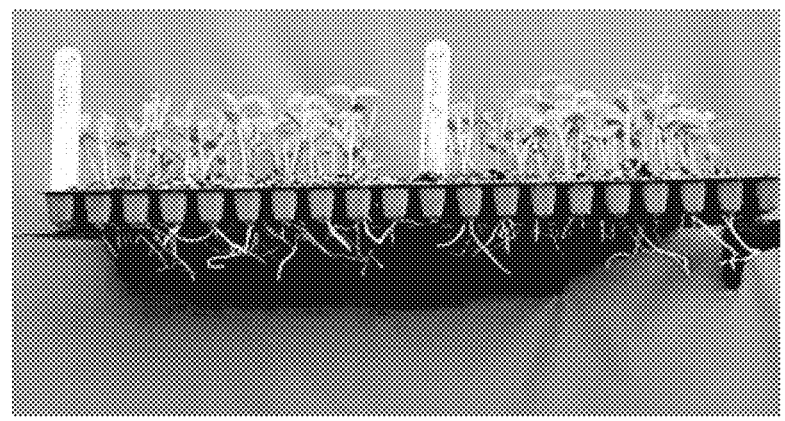
FIG. 19
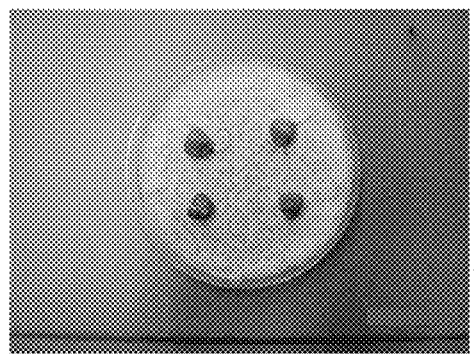 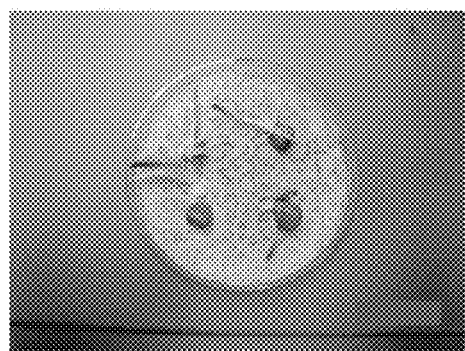
FIG. 20A  FIG. 20B

CLONOSTACHYS ROSEA INOCULATED PLANT MATERIALS WITH FUNGICIDES AND ADJUVANTS

RELATED APPLICATIONS

This application claims the benefit of U.S. Provisional Application No. 62/024,137 filed Jul. 14, 2014, which is hereby incorporated by reference.

BACKGROUND

A. Technical Field

The use of microbial inoculants to promote plant health is known. Generally, microbes, including bacteria and fungi, may be applied to a plant to improve plant nutrition, promote plant growth, provide resistance to disease and to treat disease. Examples of microbial inoculants include plant growth promoting rhizobacteria such as *Rhizobium* sp. which increase nitrogen nutrition in leguminous crops such as soybean and chickpeas, phosphate-solubilising bacteria such as *Agrobacterium radiobacter*, fungal inoculants including mycorrhizal fungi and endophytic fungi, such as *Piriformis indica*, which provide plant nutrition benefits, and composite inoculants which have shown synergistic effects on plant growth and nutrition.

An endophyte is an endosymbiont, often a bacterium or fungus, that lives within a plant for at least part of its life without causing apparent disease. Endophytes are ubiquitous and have been found in all the species of plants studied to date. Endophytes may be transmitted either vertically (directly from parent to offspring) or horizontally (from individual to unrelated individual). Vertically transmitted fungal endophytes are typically asexual and transmit from the maternal plant to offspring via fungal hyphae penetrating the host's seeds. Since their reproductive fitness is intimately tied to that of their host plant, these fungi are often mutualistic. Conversely, horizontally transmitted fungal endophytes are sexual and transmit via spores that can be spread by wind and/or insect vectors. Endophytes can benefit host plants by preventing pathogenic organisms from colonizing them. Extensive colonization of the plant tissue by endophytes creates a "barrier effect," where the local endophytes out compete and prevent pathogenic organisms from taking hold. Endophytes may also produce chemicals which inhibit the growth of competitors, including pathogenic organisms.

Various endophytes, particularly fungi, have been used in order to manage plant diseases by targeting the growth and viability of plant pathogens. In addition to their diverse utility, microbial inoculants can replace or significantly reduce the need to use harmful chemical fertilizers and pesticide treatments, which is becoming more important as regulations imposing stringent restrictions on the use of such chemicals come into force. The use of biocontrol and biostimulant fungal organisms in conventional field and horticultural crops is still relatively new. Published research has covered the use of many fungal organisms as aids in agriculture.

*Clonostachys rosea* (previously known as *Gliocladium roseum*) is recognized as a beneficial organism. *Clonostachys rosea* is a species of fungus in the family Bionectriaceae that colonizes living plants as an endophyte. *Clonostachys rosea* must be able to establish either endophytically in, or epiphytically on, plant organs, but the latter is not significant in the field (except perhaps in cases of roots), because the organism is significantly controlled by UV-A and UV-B. The use of *Clonostachys rosea* endophytes is preferable to some other biological control agents, because *Clonostachys rosea* are rapid internal colonizers, with better ability to compete against other organisms. There are a variety of *Clonostachys rosea* strains, which all share the same common features of growing quickly, having a felt-like mycelium, and having no detrimental effects on higher plants.

*Clonostachys rosea* is a locally systemic endophyte often termed translaminar, i.e. it moves from top of leaf to bottom colonizing tissue throughout the sprayed/inoculated area. Generally, there is no movement into stem or leaves from roots. A spray on flower parts may colonize seed. *Clonostachys rosea* has no sexual stage, and conidia is spread from cotyledons of soy or from inside leaves of rose that are digested and form conidia.

The modes of action of *C. rosea* as a biological control agent are not fully known, although site occupation, mycoparasitism, competition for nutrients, and secondary metabolite production have been suggested to play significant roles. The lack of understanding of the role of *Clonostachys rosea* and other endophytes in the life of plants is often dominated by the misconception that toxins or antibiotics are always involved, and the classification of endophytic organisms as biopesticides often missed the actual role in plant health.

The mode of action of *Clonostachys rosea* strains involves colonization and possession of a root system or treated portion of a plant by mycelium, followed by denial of food to other organisms. In microbial interaction, possession is 9/10ths of the law. Early colonization of seed, foliage, flowers and fruit achieves the best results.

Additionally, current research has postulated that *C. rosea* secrete hydrophobins, which are small proteins produced only by filamentous fungi, which forms amphipathic layers on the outer surface of fungal cell walls. (Dubey et al, Hydrophobins are required for conidial hydrophobicity and plant root colonization in the fungal biocontrol agent *Clonostachys rosea*, BMC Microbiology 2014, 14:18). The hydrophobic side of the amphipathic layer is exposed to the outside environment, while the hydrophilic side is directed towards cell wall polysaccharides. It has been reported that *Clonostachys rosea* can secret subtilisin-like extracellular serine proteases or potentially other substances during the infection. *C. rosea* produces the enzyme zearalenone hydrolase (ZHD101), which degrades Zearalenone ("ZEA"), which is produced by mycotoxin-producing *Fusarium* species, including *F. graminearum* and *F. culmorum*. A mycotoxin that exhibits antifungal growth. Zealerones are mycotoxins with estrogenic-mimic activity. (Kakeya, Biotransformation of the Mycotoxin, Zealerone, to a Non-estrogenic Compound by a Fungal Strain of *Clonostachys* sp., Bioscience, Biotechnology, and Biochemistry, Vol. 66 (2002) No. 12 P 2723-2726). In one case, it has been reported that pathogenesis started from the adherence of conidia to nematode cuticle for germination, followed by the penetration of germ tubes entry into the nematode body and subsequent death and degradation of the nematodes. (Zhang et al, Investigation on the infection mechanism of the fungus *Clonostachys rosea* against nematodes using the green fluorescent protein, Applied Microbiology and Biotechnology April 2008, Volume 78, Issue 6, pp 983-990).

B. Description of Related Art

*Clonostachys rosea* strains tolerate certain fungicides, and thus *Clonostachys rosea* has been considered a candidate for integrated pest management system.

Bio-priming of seeds has been well-known. See, for example, Callan, Bio-priming Seed Treatment for Biological Control of *Pythium ultimum* Preemergence Damping-off in sh2 Sweet Corn, Plant Disease, Vol. 74 No. 5 (1990); Rao, Bio-Priming Of Seeds: A Potential Tool In The Integrated Management Of *Alternaria* Blight Of Sunflower, HELIA, 32, Nr. 50, p.p. 107-114, (2009);

The published literature indicates that seeds are subjected to fungicidal treatment, followed by inoculation of a biological organism. Thus, Rao, 2009, describes that for integrated seed treatment options tested for the management of *Alternaria* blight of sunflower, the highest benefit was obtained in the seed treatment with Carbendazim+Iprodione (Quintal) at 0.3% in water along with hexaconazole foliar spray (0.1%) followed by seed treatment with *Pseudomonas fluorescens* (0.8%) in jelly+hexaconazole foliar spray.

The published literature for crops indicates that it has been generally considered that *Clonostachys rosea* is not applied together with fungicides. See for example, U.S. Pat. No. 6,495,133 to Xue who reported that "ACM941 plus 50% of the regular rate of thiram was the most effective treatment, which increased yield by 21% . . . . The results also indicated that ACM941 bioagent is compatible with thiram fungicide," and that "Results of this study also indicated that ACM941 bioagent is compatible with metalaxyl fungicide. Subsequent research by Sutton and Brown has shown that thiram and not metalaxyl is toxic to *Clonostachys rosea* ACM941. An enhanced effectiveness was generally observed when ACM941 was combined with metalaxyl fungicide." See also Macedo et al, Sensitivity of four isolates of *Clonostachys rosea* to pesticides used in the strawberry crop in Brazil, J. Pestic. Sci. 37(4), 333-337 (2012). Macedo et al determined the sensitivity of four isolates of *Clonostachys rosea* to fungicides and other pesticides, and concluded that all fungicides inhibited mycelial growth and conidia germination of all isolates. For that reason, research in the area has generally compared *Clonostachys rosea* to fungicides in side by side tests, rather than in an integrated manner. See, for example, Xue et al. Biological control of *Fusarium* head blight of wheat with *Clonostachys rosea* strain ACM941, Can. J. Plant Pathol. 31: 169-179 (2009).

An inoculant composition comprising *Clonostachys rosea* is disclosed in United States Patent Publication 20120021906A1 to Sutton and Mason. Sutton and Mason disclose a composition of a carrier having a moisture content of not more than about 5%, and a method of inoculating a plant to promote growth, enhance resistance to adverse conditions or promote re-growth is also provided comprising applying the inoculant composition to the plant.

SUMMARY

The description below provides systems and methods for effecting biocontrol in crops, and particularly includes a description of synergistic combinations of methods and microorganisms to facilitate germination and utilization of *Clonostachys rosea* for biocontrol.

The methods and microorganisms can be utilized as part of an integrated pest management program (IPM). The additional compounds or compositions may be an acaricide, a bactericide, a fungicide, an insecticide, a microbicide, a nematicide, a fertilizer, or a food preservative.

The *Clonostachys rosea* composition may be in the form of a powder, a granule, a pellet, a gel, an aqueous suspension, a solution or an emulsion. The composition may be provided with a carrier. The carrier can be a seed.

The disclosed methods and microorganisms also include examples of a method for treating, inhibiting or preventing the development of a plant pathogenic disease. The method involves applying *Clonostachys rosea* on a seed, or on or in the vicinity of a host plant. The *Clonostachys rosea* is generally established as an endophyte on the seed or plant. The integrated system combinations are particularly effective against fungal pathogens of the genus *Fusarium, Pythium* and/or *Rhizoctonia*. The pathogen causing the pathogenic disease that is controlled by the integrated system combinations may be *Aspergillus fumigatus, Botrytis cinerea, Cerpospora betae, Curvularia* sp., *Ganoderma boninense, Geotrichum candidum, Mycosphaerella fijiensis, Phytophthora palmivora, Phytophthora ramorum, Pythium ultimum, Rhizoctonia solani, Rhizopus* sp., *Schizophyllum* sp., *Sclerotinia sclerotiorum*, or *Verticillium dahlia*. For example, *Fusarium* head blight, caused by *Gibberella zeae* (syn. *Fusarium graminearum*), is one of the most important wheat diseases in Canada. The infection of wheat by the pathogen results in grain yield loss, quality reduction, and kernel contamination with deoxynivalenol (DON) and other mycotoxins. Current management of this disease relies on fungicides in most wheat production areas. Multiple fungicide applications have increased the economic cost to growers and public concerns regarding pesticide risks and pathogen resistance to fungicides. *Clonostachys rosea* is an organic alternative to the chemical or hard chemistry fungicides. In addition, preliminary laboratory and greenhouse experiments also showed that *Clonostachys rosea* (ACM941) significantly suppresses root rot, a major soybean disease caused by members of the *Fusarium* complex including *F. graminearum, F. oxysporum*, and *F. solani*.

Another further aspect of the methods and microorganisms is to provide non-naturally occurring seeds and plants infected with *Clonostachys rosea*.

In another aspect, there are provided methods for treating, inhibiting or preventing a plant pathogen-related disease. In some embodiments, the methods involve growing a culture of *Clonostachys rosea* on seeds or on or in the vicinity of the host plant, or in the growth medium or soil of the host plant prior to or concurrent with plant growth in the growth medium or soil. In one or more of the above embodiments, the method is effective to control the plant pathogen. In various embodiments, the plant pathogen is associated with the host seed or plant, or is in the growth medium or soil of the host plant prior to or concurrent with plant growth in the growth medium or soil.

Another further aspect relates to a method for killing, inhibiting or preventing the development of an undesired organism, such as a fungus, a bacterium, a microorganism, a nematode, and an insect. The method involves exposing or contacting the organism to or with an effective amount of *Clonostachys rosea* as part of the integrated management system as described below.

The protection of plant propagation materials (especially seeds) with active ingredients are target applications which partially address the need for a reduction of environmental and worker exposure when used alone or in conjunction with foliar or in-furrow active ingredient applications.

There is a continuing need to provide pesticidal combinations, which provide improved, for example, biological properties, for example, synergistic properties, especially for controlling pathogens.

The needs for an effective system for integrated pest management utilizing biocontrol are at least partially accomplished by utilizing the present disclosures. Accordingly, in a first aspect, the disclosed methods and organisms provide a pesticidal integrated treatment combination utilizing the biocontrol agent *Clonostachys rosea* in combination with chemical or hard chemistry fungicides.

The disclosed methods and organisms also provides a method of protecting a plant propagation material, a seed, plant, parts of a plant and/or plant organs that grow at a later point in time against pathogenic damage or pest damage by applying to the seed, plant, parts of plant, or their surroundings the combination, as defined in the first aspect, in a sequence. The invention also relates to a plant propagation material treated with the combination defined in the first aspect.

Further, in an embodiment the disclosed methods and organisms relates to a method which comprises (i) treating a plant propagation material, such as a seed, as defined in the first aspect, and (ii) planting or sowing the treated propagation material, wherein the combination protects against pathogenic damage or pest damage of the treated plant propagation material, parts of plant and/or plant grown from the treated propagation material.

Also, in an embodiment the disclosed methods and organisms relates to a method which comprises (i) treating a plant propagation material, such as a seed, as defined in the first aspect, and (ii) planting or sowing the treated propagation material, and (iii) achieving protection against pathogenic damage or pest damage of the treated plant propagation material, parts of plant and/or plant grown from the treated propagation material.

The biocontrol methods described here preferably and optionally comprises an adjuvant, and most preferably an adjuvant which is microencapsulated.

The pesticidal integrated combinations according to the invention have very advantageous properties for protecting plants against (i) pathogenic, such as phytopathogenic, especially fungi, attack or infestation, which result in a disease and damage to the plant and/or (ii) pest attack or damage; particularly in instance of plants, the disclosed methods and organisms can control or prevent pathogenic damage and/or pest damage on a seed, parts of plant root and/or underground or soil level portions stem of a plant grown from the treated seed.

To the accomplishment of the foregoing and related ends, certain illustrative aspects are described herein in connection with the following description and the annexed drawings. These aspects are indicative, however, of but a few of the various ways in which the principles of the claimed subject matter may be employed and the claimed matter is intended to include all such aspects and their equivalents. Other advantages and novel features may become apparent from the following detailed description when considered in conjunction with the drawings.

BRIEF DESCRIPTION OF THE DRAWINGS

FIGS. 1 through 21*b* are images that show the results of tests that are described in the Examples section of this disclosure. The description of the Figures in the Detailed Description section are incorporated herein.

FIG. 1 is a photograph showing result upon inoculation of adding different fungicides concurrently with inoculation of *Clonostachys rosea*.

FIG. 2 is a photograph showing result of adding different fungicides concurrently with inoculation of *Clonostachys rosea* applied to a fresh conidia lawn of *C. rosea* 88-710.

FIG. 3 is a photograph showing result of adding different fungicides concurrently with inoculation of *Clonostachys rosea* applied to a fresh conidia lawn of *C. rosea* ACM491.

FIG. 4 is a photograph showing result of adding different fungicides concurrently with inoculation of *Clonostachys rosea* applied to a fresh conidia lawn of *C. rosea* 88-710 taken 2 days after the paper disks were placed onto just prepared spore lawn of the fungus.

FIG. 5 is a photograph showing result of testing fungicides Quadris, Prosaro, Stratego and Tilt with *C. rosea* 88-710.

FIG. 6 is a photograph is a photograph showing result of adding different fungicides to a 48-hour old lawn of *Clonostachys rosea* upon inoculation.

FIG. 7 is a photograph showing testing of effect of fungicides on growth and conidia development of *C. rosea* 88-710 when the fungicide-treated disks were applied to a lawn of established mycelium of the fungus.

FIG. 8 is a photograph showing testing of effect of fungicides on growth and conidia development of *C. rosea* ACM491 when the fungicide-treated disks were applied to a lawn of established mycelium of the fungus.

FIG. 9 is a photograph showing testing of CruiserMaxx® Beans-coated corn seeds on the fresh spore lawn of *C. rosea* 88-710, at 2, 4 and 10 days.

FIG. 10 is a photograph showing testing of CruiserMaxx® Beans-coated corn seeds on the fresh spore lawn of *C. rosea* ACM491, at 4 and 10 days.

FIG. 11 is a photograph is a photograph showing result of adding different fungicides to a lawn of *Clonostachys rosea* 88-710.

FIG. 12 is a photograph of soybean seeds treated with CruiserMaxx® Beans applied to a PDA plate of fresh spore lawn of *C. rosea* 88-710, at 2, 6 and 10 days.

FIG. 13 is a photograph of soybean seeds treated with CruiserMaxx® Beans applied to a PDA plate of an established 48 hour old spore lawn of *C. rosea* 88-710 at 4 and 8 days.

FIG. 14 is a photograph of wheat plants grown from seeds sprayed with 10 ml water/Kg of wheat seed, without any inoculation, with left half without drying and right half air dried after 24 hours and then placed into plastic bag.

FIG. 15 is a photograph of wheat plants grown from seeds sprayed with 10 ml of *Clonostachys rosea* suspension/Kg of wheat seed, without C-Wet, with left half without drying and right half air dried after 24 hours and then placed into plastic bag.

FIG. 16 is a photograph of wheat plants grown from seeds sprayed with 10 ml of *Clonostachys rosea* suspension/Kg of wheat seed, with C-Wet adjuvant, with left half without drying and right half air dried after 24 hours and then placed into plastic bag.

FIG. 17 is a photograph of soybean plants grown from seeds sprayed with 10 ml water/Kg of seed, without any inoculation, with left half without drying and right half air dried after 24 hours and then placed into plastic bag.

FIG. 18 is a photograph of soybean plants grown from seeds sprayed with 10 ml of *Clonostachys rosea* suspension/Kg of seed, without C-Wet, with left half without drying and right half air dried after 24 hours and then placed into plastic bag.

FIG. 19 is a photograph of soybean plants grown from seeds sprayed with 10 ml of *Clonostachys rosea* suspension/

Figure 1:
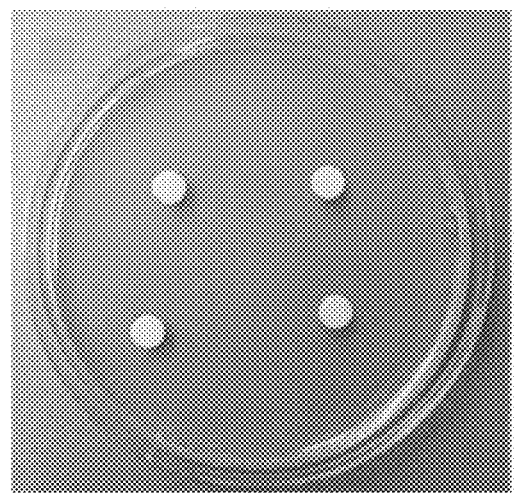

Kg of seed, with C-Wet adjuvant, with left half without drying and right half air dried after 24 hours and then placed into plastic bag.

FIG. 20*a* is a photograph CruiserMaxx® Beans treated seed corn was placed on mature *C. rosea* ACM941 mycelium after 4 days.

FIG. 20*b* is a photograph CruiserMaxx® Beans treated seed corn was placed on mature *C. rosea* ACM941 mycelium after 10 days.

FIG. 21*a* is a photograph CruiserMaxx® Beans treated seed corn was placed on mature *C. rosea* 88-710 mycelium after 4 days.

FIG. 21*b* is a photograph CruiserMaxx® Beans treated seed corn was placed on mature *C. rosea* 88-710 mycelium after 10 days.

DETAILED DESCRIPTION

Definitions

The below terms used in this disclosure are defined as follows:

"biological control" means control of a pathogen or any other undesirable organism by the use of a second organism. An example of a known mechanism of biological control is the use of microorganisms that control root rot by out-competing fungi for space on the surface of the root, or microorganisms that either inhibit the growth of or kill the pathogen. The "host seed" or "host plant" in the context of biological control is the seed or plant that is susceptible to disease caused by the pathogen. In the context of isolation of an organism, such as a fungal species, from its natural environment, the "host seed" or "host plant" is a seed or plant that supports the growth of the fungus, for example, a seed or plant of a species with an endophytic relationship with *Clonostachys rosea.*

"composition" means a combination of one or more active agents and/or another compound, carrier or composition, inert (for example, a detectable agent or label or liquid carrier) or active, such as a pesticide.

"control," "protecting" and their inflections mean reducing any undesired effect, such as pathogenic, such as phytopathogenic, especially fungi, infestation or attack of, and pathogenic damage or pest damage on, a plant, part of the plant or plant propagation material to such a level that an improvement is demonstrated.

"culturing" means the propagation of organisms on or in media of various kinds.

"effective amount" means an amount sufficient to affect beneficial or desired results. An effective amount can be administered in one or more administrations. In terms of treatment, inhibition or protection, an effective amount is that amount sufficient to ameliorate, stabilize, reverse, slow or delay progression of the target infection or disease states.

"fungicidal" means the ability of a substance to decrease the rate of growth of fungi or to increase the mortality of fungi.

"fungus" or "fungi" is meant to include a wide variety of nucleated spore-bearing organisms that are devoid of chlorophyll. Examples of fungi include yeasts, molds, mildews, rusts, and mushrooms.

"innoculation" means the addition of *Clonostachys rosea* cells to plant propagation material.

"cultivated plants" means any plants which are grown where desired or planted, and include both native plants and plants which have been modified by breeding, mutagenesis or genetic engineering.

"plant propagation material" means all the generative parts of the plant such as seeds and vegetative plant material such as cuttings and tubers, which can be used for the multiplication of the plant. This includes seeds, roots, fruits, tubers, bulbs, rhizomes, shoots, sprouts and other parts of plants, including seedlings and young plants, which are to be transplanted after germination or after emergence from soil.

"plant" is a term that includes both cultivated plants and plant propagation materials.

BRIEF OVERVIEW

The disclosed methods and organisms help resolve the two fold challenge to widespread use of living fungal biostimulants or biopesticides, which are:

1. Colonization or establishment of the organism inside a plant; and

2. Tolerance or the ability to use the beneficial microbes with traditional hard chemistry fungicides and insecticides in an integrated pest management (IPM) system.

*Clonostachys rosea* is useful in controlling pathogens. However, *Clonostachys rosea* by itself may not completely control pathogenic fungi. Unfortunately, *Clonostachys rosea* strains generally show a lack of tolerance to many conventional chemical fungicides, and there is always a significant risk that in any particular environmental set of conditions a fungicide may be deleterious. For example, in greenhouse experiments, *Clonostachys rosea* demonstrated in vitro tolerance to the fungicide Switch®, but little or no tolerance to Pristine® and Maestro®. See, for example, Reeh et al, Laboratory efficacy and fungicide compatibility of *Clonostachys rosea* against *Botrytis* blight on lowbush blueberry, Canadian Journal of Plant Science, 2013, 93(4): 639-642; Xue 2003, supra. Thus, use of conventional chemical fungicides can become fundamentally problematic when *Clonostachys rosea* is utilized, because, absent proper application as provided herein, the fungicide can harm, if not essentially destroy, the *Clonostachys rosea.*

It has now been discovered that *Clonostachys rosea* may be safely used in combination with chemical fungicides as both a seed treatment and the field, when seeds and/or plants are first inoculated with *Clonostachys rosea*, followed by treatment with a fungicide about 48 hours later upon the establishment of *Clonostachys rosea* mycelia. Fungicides have significantly greater effectiveness against *Clonostachys rosea* conidia than mycelia. Further, generally, development of mycelia corresponds to tolerance to fungicides. Thus, *Clonostachys rosea* mycelium once inside seeds or plants about a week after inoculation have greater or increased tolerance to fungicides than after only about two days.

*Clonostachys rosea*

Any species or strain of *Clonostachys rosea* may be used in the disclosed methods and organisms. *C. rosea* ACM941 and 88-710 strains have been found to be particularly useful. *Clonostachys rosea* is commercially available under the trademark EndoFine® (available from Adjuvants Plus Inc., Kingsville, Ontario N9Y2Y8).

The invention compositions comprising the culture of *Clonostachys rosea* can be in a variety of forms, including, but not limited to, still cultures, whole cultures, stored stocks of mycelium and/or hyphae (particularly glycerol stocks), agar strips, stored agar plugs in glycerol/water, freeze dried stocks, and dried stocks such as mycelia dried onto filter paper or on or inoculated into live or sterilized grain seeds.

The disclosure further provides a composition that includes *Clonostachys rosea* and a carrier. The carrier may be any one or more of a number of carriers that confer a variety of properties, such as increased stability, wettability, dispersability, etc. Wetting agents such as natural or synthetic surfactants, which can be nonionic or ionic surfactants, or a combination thereof can be included in a composition of the invention. Suitable formulations that may be prepared include wettable powders, granules, gels, agar strips or pellets, thickeners, and the like, microencapsulated particles, and the like, liquids such as aqueous flowables, aqueous suspensions, water-in-oil emulsions, etc. The formulation may include grain or legume products (e.g., ground grain or beans, broth or flour derived from grain or beans), starch, sugar, or oil. The carrier may be an agricultural carrier. In certain embodiments the carrier is a seed, and the composition may be applied or coated onto the seed or allowed to saturate the seed.

The agricultural carrier may be soil or plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers. Formulations may include food sources for the cultured organisms, such as barley, rice, or other biological materials such as seed, plant parts, hulls or stalks from grain processing, ground plant material ("yard waste") or wood from building site refuse, sawdust or small fibers from recycling of paper, fabric, or wood. Other suitable formulations will be known to those skilled in the art.

The invention contemplates that different strains *Clonostachys rosea* may be used to inoculate plants simultaneously or sequentially. Such combination of *Clonostachys rosea* may provide a broader spectrum of activity and protection to the plant.

Fungicides

A wide variety of fungicides can be used with the disclosed methods and organisms. Examples of azole type fungicides are thiabendazole, oxpoconazole, ipconazole and prothioconazole; especially preferred are thiabendazole, ipconazole and prothioconazole. Examples of phenylamide type fungicides include mefenoxam (metalaxyl-M), metalaxyl, benalaxyl, benalaxyl-M, oxadixyl and furalaxyl. Examples of strobilurin fungicides are azoxystrobin, picoxystrobin, metominostrobin, pyraclostrobin, famoxadone, fenamidone, fluoxastrobin, kresoxim-methyl, and trifloxystrobin. Examples of phenylpyrrole fungicides are fenpiclonil and fludioxonil. Potentially useful fungicides also include cyclic bisoxime derivatives described in United States Patent Publication 20140162980A1 to Stierli; the N-cycloalkyl-N-biphenylmethyl-carboxamide derivatives described in United States Patent Publication 20140171474A1 to Desbordes et al, the disclosure of which is incorporated here by reference; the pyrazole carboxamides derivatives described in United States Patent Publication 20140148411 A1 to Bartels et al, the disclosure of which is incorporated here by reference;

The fungicides may also be used in combination of fungicides, as described in United States Patent Publication 20140148338A1 to Hoffmann et al, the disclosure of which is incorporated here by reference.

Seed Inoculation and Treatment

The invention is useful as method of inoculating and treating seeds to prevent pathogenic activity and to improve crop yields. The invention furthermore relates to seed treated according to the descriptions herein. A large part of the damage to crop plants caused by harmful organisms is triggered by an infection of the seed during storage or after sowing as well as during and after germination of the plant, because the roots and shoots of the growing plant are particularly sensitive, and even small damage to the growing roots may result in damaging the plant. Accordingly, there is great interest in protecting the seed prior to sowing.

The control of phytopathogenic fungi by treating the seed of plants has been known for a long time, but can still be improved. One of the advantages of the disclosed methods and organisms is that, because of the particular properties of the compositions according to the invention, treatment of the seed with these compositions not only protects the seed at harvest through planting after planting, and for the remainder of the season from phytopathogenic fungi. In this manner, the immediate treatment of the crop at the time of sowing or shortly thereafter can be dispensed with. The disclosed methods and organisms may potentially permit farmers to dispense with the additional application of crop protection agents at sowing. Thus, the invention further optimizes the amount and effect of *Clonostachys rosea* and fungicidal active ingredients employed to provide maximum protection for the seed and the germinating plant from attack by phytopathogenic fungi, without damaging the plant itself by the active compound employed.

Methods for applying or treating pesticidal active ingredients and mixtures thereof on to plant propagation material, especially seeds, are known in the art, and include dressing, coating, pelleting and soaking application methods of the propagation material. It is preferred that the plant propagation material is a seed.

The active ingredients can be applied to the *C. rosea* inoculated seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In one embodiment, the combination is applied on to seeds in an amount and by a method such that the germination of the seed is not induced, and that the seed is not adversely affected, or that the resulting plant is not damaged. This must be borne in mind in particular in the case of active compounds which may have phytotoxic effects at certain application rates. Generally seed soaking induces germination because the moisture content of the resulting seed is too high.

The compositions according to the invention can be applied directly as a dust to seed, that is to say without comprising further components and without having been diluted. In general, it is preferable to apply the compositions to the seed in the form of a suitable formulation. Suitable formulations and methods for the treatment of seed are known to the person skilled in the art and are described, for example, in the following documents: U.S. Pat. Nos. 4,272,417; 4,245,432; 4,808,430; and 5,876,739; and Publications 2003/0176428 A1, WO 2002/080675A1, and WO 2002/028186A2.

Accordingly, examples of suitable methods for applying (or treating) a plant propagation material, such as a seed, is seed dressing, seed coating or seed pelleting and alike.

It is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would induce endophytic activity of *Clonostachys rosea*, but cause no biological damage to the seed. It is believed that the *Clonostachys rosea* treatment can be applied to the seed at any time between harvest of the seed and sowing of the seed, but preferably before the sowing process.

Even distribution of the *Clonostachys rosea* active and subsequent fungicide ingredients and their adherence to the seeds is desired during seed integrated combination treatment. Application could vary from a thin film (dressing) of the formulation containing the active ingredient(s) on a seed, where the original size and/or shape are recognizable to an intermediary state (such as a coating) and then to a thicker film (such as pelleting with many layers of different materials (such as carriers, for example, clays; different formulations, such as of other active ingredients; polymers; and colorants) where the original shape and/or size of the seed is no longer recognisable. As a result of the combined applications, the active ingredients in the combination are adhered on to the seed and therefore available for pest and/or disease control. The treated seeds can be stored, handled, sowed and tilled in the same manner as any other active ingredient treated seed.

The integrated system combination according to the disclosed methods and organisms is suitable for seeds of the crops: maize (corn), rice, coffee, cereals (wheat, barley, rye, oats, corn, rice, sorghum, triticale and related crops); beet (sugar beet and fodder beet); leguminous plants (beans, lentils, peas, soybeans); oil plants (rape, mustard, sunflowers); cucumber plants (marrows, cucumbers, melons); fibre plants (cotton, flax, hemp, jute); vegetables (spinach, lettuce, asparagus, cabbages, carrots, onions, tomatoes, potatoes, paprika); as well as lawn and ornamental plants (flowers, shrubs, broad-leafed trees and evergreens, such as conifers). Especially suitable are seeds of wheat, barley, rye, oats, triticale, sorghum, corn, and soybean; each combination is advantageously preferred for the crops sorghum, corn and soybean. The compositions according to the invention are suitable for protecting seed of any plant variety employed in agriculture, in the greenhouse, in forests or in horticulture or viticulture. (also see below).

The seeds or other plant propagation material treated by an integrated system combination of the disclosed methods and organisms are, therefore, resistant to disease and/or pest damage; accordingly, the disclosed methods and organisms also provides a pathogenic and/or pest resistant plant propagation material which is treated with the combination and consequently at least the active ingredients thereof are adhered on the propagation material, such a seed.

The integrated system seed treatment combination and compositions can also comprise or may be applied together with other active compounds, where the *Clonostachys rosea* and a fungicide are applied sequentially with at least about 48 hour differential, and where other pesticidal active ingredients are applied in combination with the fungicide, although the non-fungicidal active ingredients can be applied to the seed at any time.

The non-fungicidal pesticidal active ingredient may have activity in more than area of pest control, for example, a pesticide may have insecticide and nematicide activity.

A seed coating or seed dressing formulation can be applied to the seeds in sequence employing the compositions of the invention and a diluent in suitable seed coating formulation form, e.g. as an aqueous suspension or in a dry powder form having good adherence to the seeds. Such seed coating or seed dressing formulations are known in the art. Such formulations may contain the single active ingredients or the combination of active ingredients in encapsulated form, e.g. as slow release capsules or microcapsules.

It has been found that seeds inoculated with *Clonostachys rosea* as EndoFine® SI will remain viable for more than four years if stored in cool conditions (35° F. to 41° F.).

The seeds are preferably inoculated by *Clonostachys rosea* within a short period after harvest, such as for example, within a two days or a week after harvest, although seeds can also be treated a month or six weeks or some months or even years after harvest. The earlier the inoculation the more likely that the seeds will obtain the benefits of the inoculation, and particularly if the seeds are inoculated before seed treatment and coating or pelletizing.

A typical application rate of *Clonostachys rosea* to seed as a liquid suspension is 10 grams per liter of water as the suspension mix and 10 mls of that suspension (1 to $2 \times 10^7$ CFU) would be used to inoculate a kilogram of seed. A typical dry application to seed would be 0.5 to 1 gram per kilogram. A typical foliar application range would be 300 to 1850 grams per hectare depending on crop size and weather conditions up to and including mature fruit and nut trees.

Soil and Plant Applications

The invention provides methods for preventing or treating a plant-pathogen-related disease, in which the method includes applying a composition comprising one or more *Clonostachys rosea* organisms to soil or a plant growth medium. A non-soil plant growth medium can be sand, vermiculite, fibers, a gel or liquid based medium for plant growth, etc. In some embodiments, the soil or plant growth medium treated with a *Clonostachys rosea* composition contains seeds of plants of one or more plants of a species of interest. In some embodiments, soil or another plant growth medium is treated with a *Clonostachys rosea* composition and is subsequently planted with one or more plants of a species of interest. The planting can be of seeds, shoots, roots, or transplanting of whole plants (such as, but not limited to, seedlings). The *Clonostachys rosea* composition can be mixed into the soil or growth medium, bored or injected into the soil or growth medium, sprayed, drenched, dusted, or scattered on the soil or growth medium, and optionally watered in.

The invention thus provides a method to use compositions of *Clonostachys rosea* to kill plant pathogens in soil. Suitable formulations for soil treatment are apparent to those of skill in the art and include wettable powders, granules, pellets, and the like, encapsulations in a suitable medium and the like, liquids such as aqueous flowables and aqueous suspensions, and emulsifiable concentrates. Formulations may include food sources for the cultured organisms, such as barley, rice, or other organic materials such as empty fruit bunches.

The composition containing *Clonostachys rosea* may be turned into the soil prior to the planting of a crop or during the planting of seeds, roots, or shoots, or transplanting of plants, or the composition can be applied to the soil after plants have been established. The composition may also be directly applied to the roots of the plants. The plants in some embodiments have root disease caused by a plant pathogen.

The invention utilizes the characteristic of *Clonostachys rosea* strains of rapid germination of conidia, and the new understanding of the role of conidia in colonization and the influence of the hydrophobic nature of conidia on colonization for *Clonostachys rosea* species.

Adjuvants

Suitable wetting agents that may be present in the seed dressing formulations which can be used according to the invention include all substances which promote wetting and are customary in the formulation of active agrochemical substances, provided that care is applied to either avoid any adjuvants that can harm or kill *Clonostachys rosea* in solution or by use of microencapsulation which results in a surfactant that is safe in the dry product as well as safe in the spray tank As to the fungicide or other non-*Clonostachys rosea* active ingredients, the invention encompasses, depending upon the nature of the active ingredient compounds to be formulated, suitable surface-active compounds are non-ionic, cationic and/or anionic surfactants having good emulsifying, dispersing and wetting properties. The term "surfactants" will also be understood as comprising mixtures of surfactants. Advantageous application-promoting adjuvants are also natural or synthetic phospholipids of the cephalin and lecithin series, e.g., phosphatidylethanolamine, phosphatidylserine, phosphatidylglycerol and lysolecithin. Generally, suitable dispersants and/or emulsifiers that may be present in the fungicidal portion of the seed dressing formulations which can be used according to the invention include all nonionic, anionic, and cationic dispersants which are customary in the formulation of active agrochemical substances. Particularly suitable nonionic dispersants are ethylene oxide-propylene oxide block polymers, alkylphenol polyglycol ethers, and tristyrylphenol polyglycol ethers, and their phosphated or sulphated derivatives. Particularly suitable anionic dispersants are lignosulphonates, polyacrylic salts, and arylsulphonate-formaldehyde condensates. Defoamers that may be present in the fungical or other non-*Clonostachys rosea* seed dressing formulations to be used according to the invention include all foam-inhibiting compounds which are customary in the formulation of agrochemically active compounds. Preference is given to using silicone defoamers, magnesium stearate, silicone emulsions, long-chain alcohols, fatty acids and their salts and also organofluorine compounds and mixtures thereof. Preservatives that may be present in the seed dressing formulations to be used according to the invention include all compounds which can be used for such purposes in agrochemical compositions. By way of example, mention may be made of dichlorophen and benzyl alcohol hemiformal. Secondary thickeners that may be present in the seed dressing formulations to be used according to the invention include all compounds which can be used for such purposes in agrochemical compositions. Preference is given to cellulose derivatives, acrylic acid derivatives, polysaccharides, such as xanthan gum or Veegum, modified clays, phyllosilicates, such as attapulgite and bentonite, and also finely divided silicic acids. Suitable adhesives that may be present in the seed dressing formulations to be used according to the invention include all customary binders which can be used in seed dressings.

Formulations of natural biocontrol agents such as *Clonostachys rosea* present different challenges. Microencapsulated adjuvants improve the speed of an already quick germinating conidia facilitating more rapid colonization and broaden the conditions of use. Particularly useful are microencapsulated adjuvants within dry conidia based formulations or added at the time of spraying. The most preferred microencapsulated adjuvants are those that have been developed by Dr. Gary Harman of Cornell University, and disclosed in U.S. application Ser. No. 14/407,868, the disclosure of which is incorporated by reference. In particular, it has been discovered that cyclodextrins provide a useful formulation tool. These are circularized glucose moieties of 6-8 units; the center of the cyclodextrin molecule is hydrophobic and so form inclusion complexes with hydrophobic molecules including those useful for *Clonostachys rosea* formulations. The interior hydrophobic portion of the molecule effectively sequesters oleophilic molecules, holds them in this center and releases them when water is present. This permits production of a stable formulation which limits release of volatile materials and sequesters materials such as surfactants that would otherwise damage *Clonostachys rosea*. Cyclodextrins are unaffected by shear forces and readily disperse for use in liquid products. U.S. application Ser. No. 14/407,868 describes formulations of *Clonostachys rosea* in Examples 4 and 5, which are incorporated by reference.

Thus, following Ser. No. 14/407,868, there is provided a unique and novel liquid suspension made by a process of combining or mixing a cyclodextrin or other dextrin and *Clonostachys rosea* at different ratios, with higher ratios of *Clonostachys rosea* to dextrin providing a greater percentage of free and loosely attached *Clonostachys rosea* than lower ratios. In this composition, the cyclodextrin or other dextrin and *Clonostachys rosea* interact, and some of the cyclodextrin is mixed with, but does not directly interact with, *Clonostachys rosea*.

The most preferred adjuvant for *Clonostachys rosea* is C-Wet™ (available from Adjuvants Plus Inc., Kingsville, Ontario N9Y2Y8), which is an encapsulated dry powder adjuvant made from cyclodextrin captured siloxane polyalkyleneoxide copolymer in the ratio of approximately 10:3, and made consistently with U.S. application Ser. No. 14/407,868.

EXAMPLES

Comparative Example 1

The effect of adding different fungicides concurrently with inoculation of *Clonostachys rosea* was tested.

Potato dextrose agar ("PDA") plates were inoculated. In one set of experiments, the PDA plates were inoculated with *C. rosea* 88-710 and in a second set of experiments with ACM941. Filter paper disks (7 mm in diameter) were soaked with the working solution of each fungicide tested (see Table 1 below). The four disks of the fungicide-soaked disks were placed onto the spore lawn of *C. rosea* immediately after the PDA plates were inoculated with the *Clonostachys rosea* conidia.

TABLE 1

| | | Prepared 10 ml of working solution | | Concentrations of the |
| --- | --- | --- | --- | --- |
| Fungicides | The field use rates | SD water (µl) | Fungicide (µl) | working solution (%, v/v) |
| Folicur- tebuconazole group 3 | 292 ml/ha | 9970(9.970 ml) | 30 | 0.3 |
| Tilt 250 E- propiconazole group 3 | 250-500 ml/ha | 9950(9.950 ml) | 50 | 0.5 |
| Prosaro 250 g/L- tebuconazole group 3 | 800 mL/ha | 9920(9.920 ml) | 80 | 0.8 |
| Caramba 90 g/L metconazole group 3 | 500-700 ml/ha | 9930(9.930 ml) | 70 | 0.7 |

TABLE 1-continued

| Fungicides | The field use rates | Prepared 10 ml of working solution | | Concentrations of the working solution (%, v/v) |
| --- | --- | --- | --- | --- |
| | | SD water (µl) | Fungicide (µl) | |
| Acapela 250 g/L- picoxystrobin group 11 | 600 to 800 ml/ha | 9920(9.940 ml) | 80 | 0.8 |
| Headline EC - pyraclostrobin group 11 | 300-600 ml/ha | 9940(9.940 ml) | 60 | 0.6 |

The PDA plates upon inoculation are shown in FIG. 1. There were 3 replicate plates for each treatment.

Figure 2:
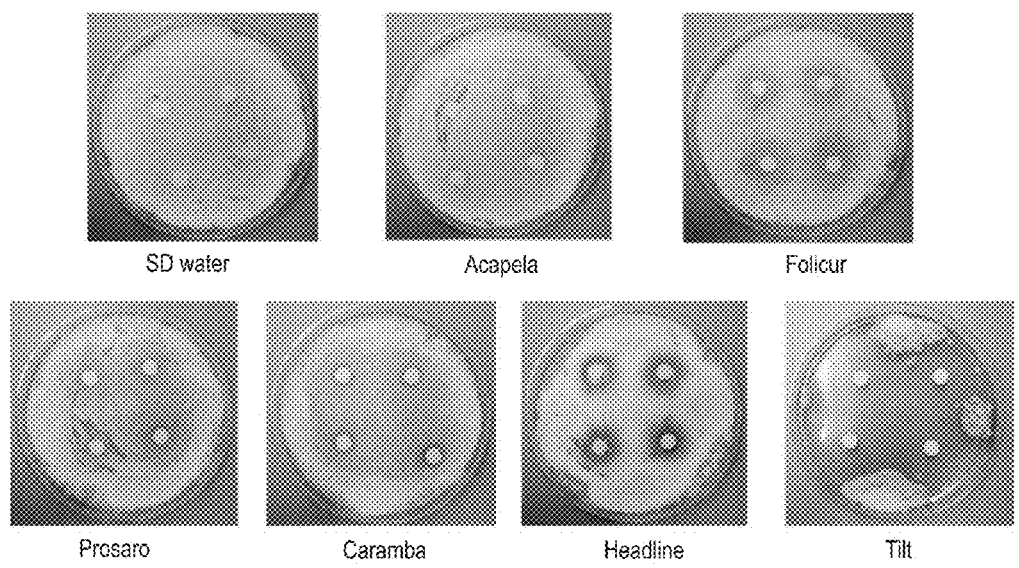
Figure 3:
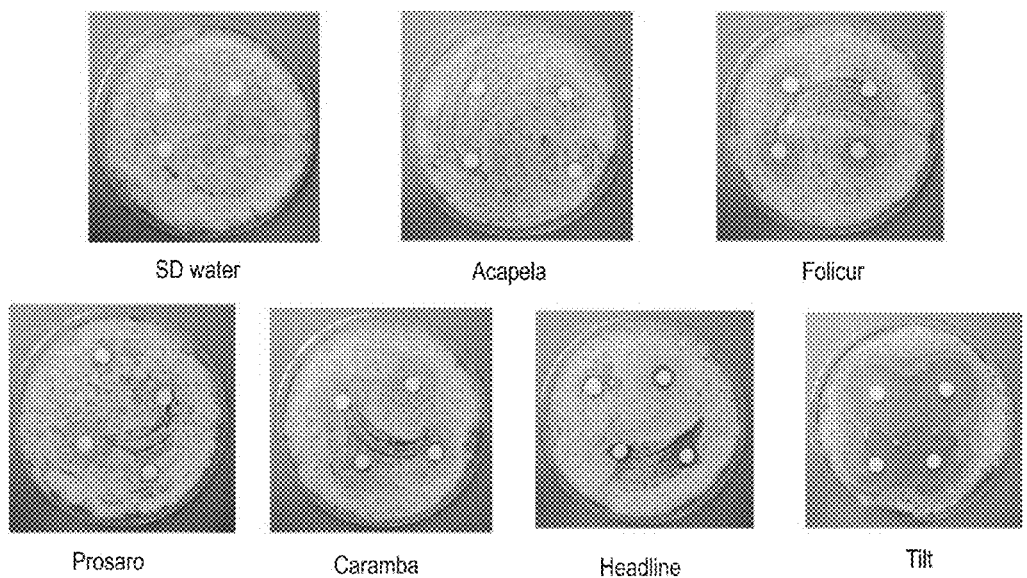
Figure 4:
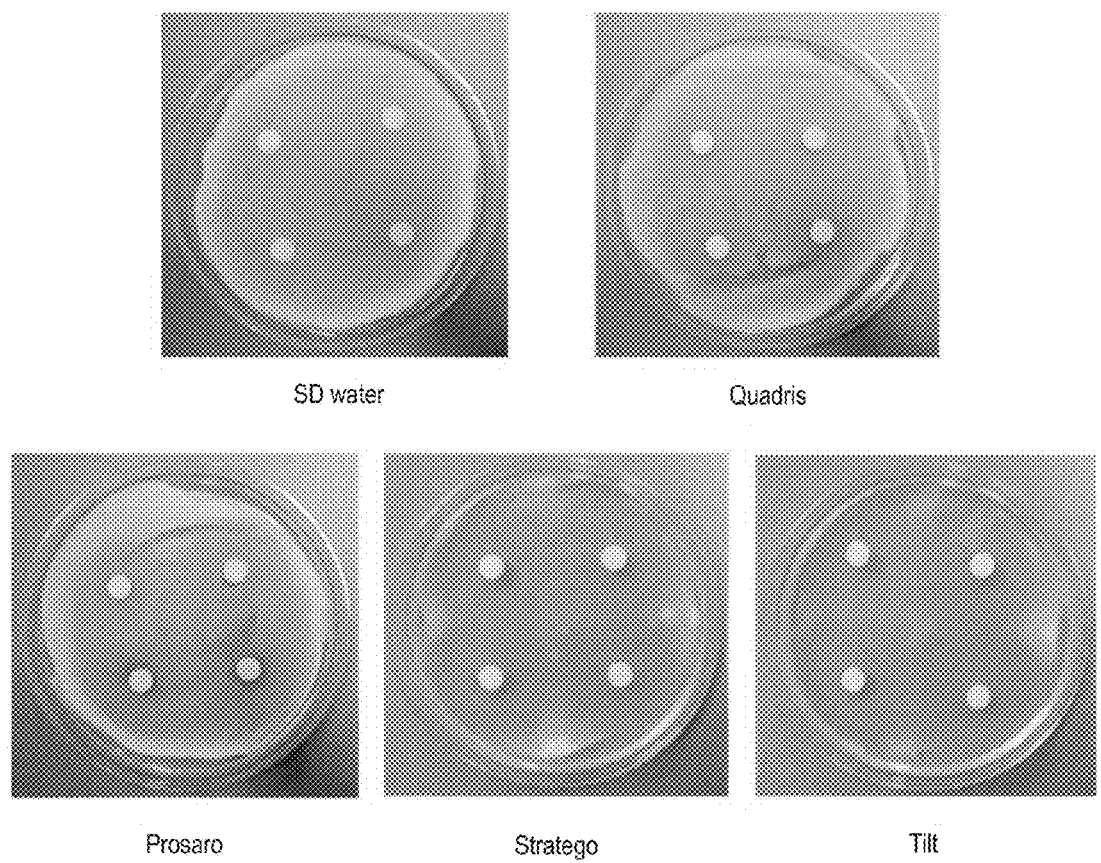

The results of the experiments are shown in Tables 2 and 3, and FIGS. 2, 3 and 4. Table 2 shows the mean diameter of inhibition zones of two isolates of *C. rosea* (in mm±S.E.) surrounding fungicide-treated filter paper disks after 2, 4, and 6 days of incubation. The disks were placed on the medium immediately after conidia of *C. rosea* were spread onto the medium. Table 3 shows the mean diameter of inhibition zones of two isolates of *C. rosea* 88-710 (in mm±S.E.) surrounding fungicide-treated filter paper disks after 2 and 6 days of incubation. The disks were placed on the medium immediately after conidia of *C. rosea* were spread onto the medium. Table 3 includes also soybean seeds as a control. All tests include sterilized distilled ("SD") water as a control.

suppressed *C. rosea* germination and growth (33 mm clear zones of inhibition of germination; no growth back over clear zones). Other fungicides produced inhibition zones from 20 to 31 mm in diameter (Table 2). Folicur did not inhibit spore germination (no clear zones) but showed some inhibition mycelial growth and sporulation. Prosaro, Caramba and Headline produced clear zones 1 to 5 mm away from the disks. Headline completely suppressed sporulation of *C. rosea* 88-710, but not of ACM941. In inhibition zones, 88-710 sporulated mainly via verticillate conidiophores while ACM941 produced mainly penicillate conidiophores; this may indicate that ACM941 is marginally more resistant to the tested fungicides than is 88-710. In the photographic record of the assay plates presented in FIGS. 2 and 3, compatibility of *C. rosea* with the tested fungicides is presented in order from the most to the least compatible.

TABLE 2

| *C. rosea* isolate | Fungicides | Day after fungicide applied | | |
| --- | --- | --- | --- | --- |
| | | 2 | 4 | 6 |
| 88-710 | CruiserMaxx ® Beans | 22.0 ± 1.19 C a | 19.9 ± 1.50 C a | 16.0 ± 2.67 D b |
| | Folicur | 22.5 ± 0.44 C a | 20.7 ± 0.28 C a | 20.7 ± 0.68 C a |
| | Tilt 250 E | 32.8 ± 0.41 A a | 32.8 ± 0.37 A a | 32.5 ± 0.40 A a |
| | Prosaro | 21.9 ± 0.53 C a | 19.4 ± 0.53 C a | 21.6 ± 0.63 C a |
| | Caramba | 31.2 ± 0.58 A a | 26.5 ± 0.48 B a | 27.8 ± 0.68 B b |
| | Acapela | 0.0 D a | 0.0 E a | 0.0 E a |
| | Headline EC | 25.6 ± 0.62 B a | 14.6 ± 0.80 D b | 14.0 ± 0.85 D b |
| ACM941 | CruiserMaxx ® Beans | 21.9 ± 0.88 C a | 19.9 ± 0.56 C a | 14.7 ± 2.06 D b |
| | Folicur | 20.7 ± 0.26 CD a | 21.3 ± 0.61 C a | 20.1 ± 0.50 C a |
| | Tilt 250 E | 33.6 ± 0.68 A a | 32.8 ± 0.73 A a | 31.7 ± 0.71 A a |
| | Prosaro | 19.1 ± 0.70 D b | 21.9 ± 0.80 C a | 23.7 ± 0.89 B a |
| | Caramba | 20.8 ± 0.37 CD c | 26.3 ± 0.81 B a | 24.0 ± 0.54 B b |
| | Acapela | 0.0 E a | 0.0 D a | 0.0 F a |
| | Headline EC | 24.7 ± 0.54 B a | 24.8 ± 0.95 B a | 11.7 ± 0.19 E b |

Note:
Values in the same column within the isolate with different the upper case letters differ significantly (p ≤ 0.05).
Values in the same row with the different lower case letters differ significantly (p ≤ 0.05).

TABLE 3

| Fungicides | Day after fungicide applied | |
| --- | --- | --- |
| | 2 | 6 |
| Tilt 250 E | 35.0 ± 0.87 A a | 33.8 ± 0.72 A a |
| Prosaro | 25.0 ± 0.37 B a | 24.4 ± 0.29 C a |
| Quadris | 25.1 ± 0.36 B a | 24.5 ± 0.29 C a |
| Stratego | 35.2 ± 0.17 A a | 31.0 ± 0.56 B b |
| Soybean seeds | 20.8 ± 0.93 C a | 21.7 ± 1.22 D a |

FIG. 2 documents the results of the tested fungicides applied to a fresh conidia lawn of *C. rosea* 88-710. FIG. 3 documents the results of the tested fungicides applied to a fresh conidia lawn of *C. rosea* ACM941. In both cases, the images were taken two days after the paper disks were applied to the PDA plates.

Acapela did not visibly affect germination and growth the *C. rosea* isolates (no clear zones). Tilt 250E markedly Compatibility was based on size of inhibition zones, clear zones around the disks and sporulation of *C. rosea*.

Figure 4A:
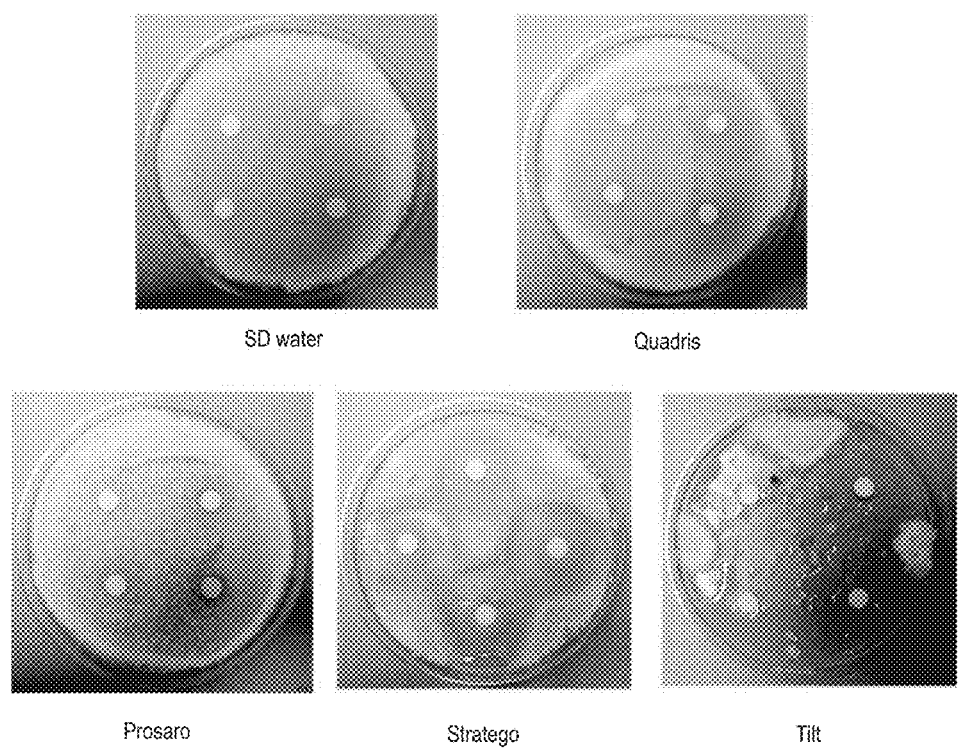
FIG. 4*a* is a photograph showing result of adding different fungicides concurrently with inoculation of *Clonostachys rosea* applied to a fresh conidia lawn of *C. rosea* 88-710 taken 10 days after the paper disks were placed onto just prepared spore lawn of the fungus.
Figure 5:
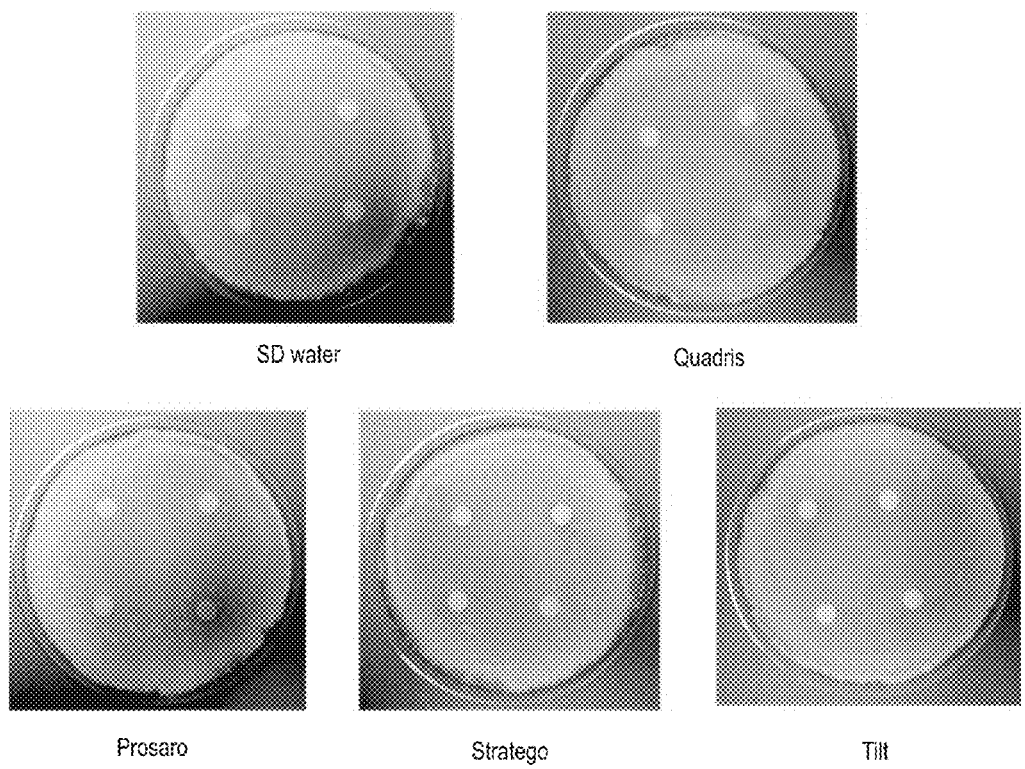

FIG. 4 documents the results of the tested fungicides applied to a fresh conidia lawn of *C. rosea* 88-710. The photos were taken 2 days after the paper disks were placed onto just prepared spore lawn of the fungus. FIG. 4a shows the compatibility, from the most to the least, of *C. rosea* 88-710 with the tested fungicides. The photos were taken 10 days after the paper disks were placed onto just prepared spore lawn of the fungus. As Stratego and Tilt inhibited *C. rosea* growth, contaminated bacteria started growth on the uncovered area FIG. 5 shows that tested fungicides (Quadris, Prosaro, Stratego and Tilt) had little or no effect on growth and sporulation of *C. rosea* 88-710 when the fungicide-treated disks were applied to a lawn of established mycelium the fungus.

Example 2

The method of Comparative Example 1 was followed, except the four disks of the fungicide-soaked disks were placed onto the spore lawn of *C. rosea* 48 hours after the PDA plates were inoculated with the *Clonostachys rosea* spores.

Figure 6:
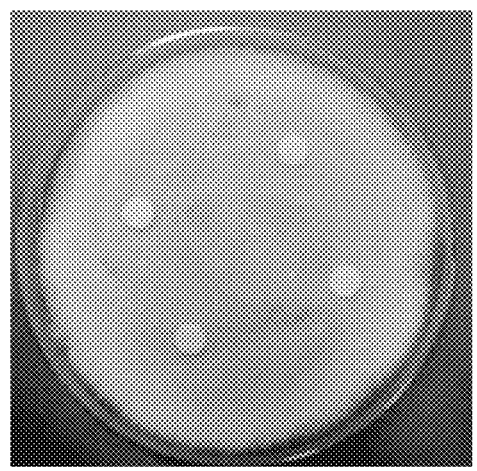
Figure 7:
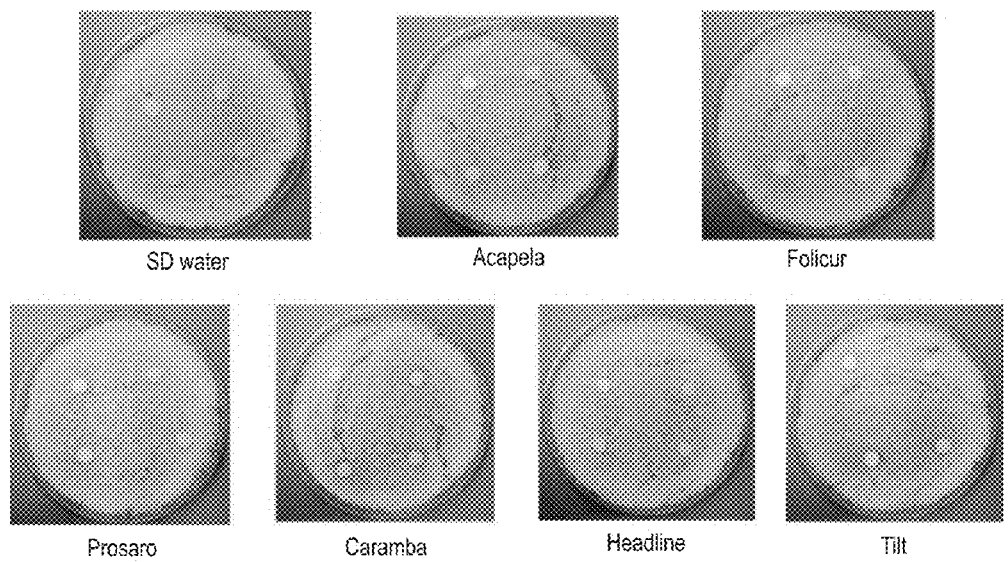
Figure 8:
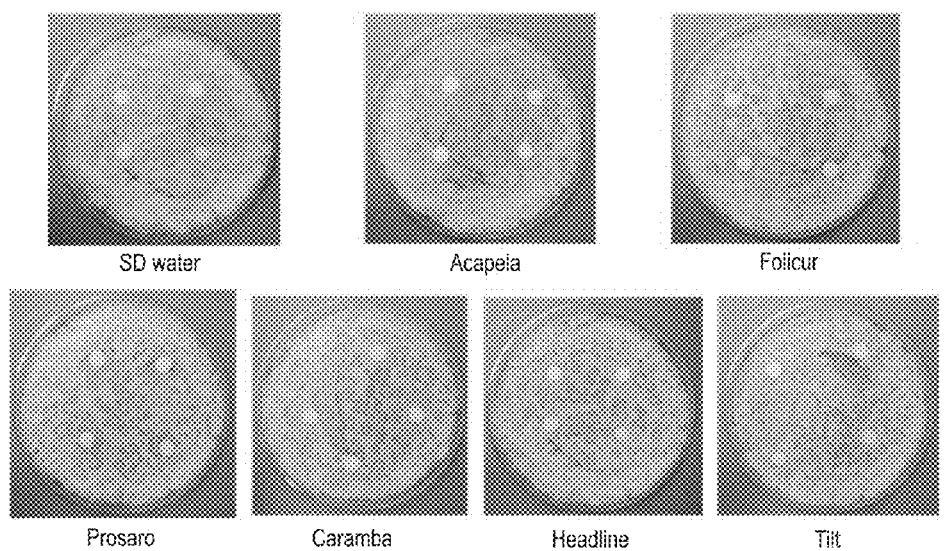

The PDA plates upon inoculation are shown in FIG. 6. The results of the experiments are shown in FIGS. 7 and 8. FIG. 7 documents the results of the tested fungicides applied to a 48-hour old lawn of *C. rosea* 88-710. FIG. 8 documents the results of the tested fungicides applied to a 48-hour old lawn of *C. rosea* ACM941. In both cases, the images were taken 2, 4, 6 and 10 days after the paper disks were applied to the 48 hour old lawn on PDA plates.

FIG. 7 shows that the tested fungicides showed little or no effect on growth and conidia development of *C. rosea* 88-710 when the fungicide-treated disks were applied to a lawn of established mycelium of the fungus. FIG. 8 shows that the tested fungicides showed little or no effect on growth and conidia development of *C. rosea* ACM 941 when the fungicide-treated disks were applied to a lawn of established mycelium of the fungus.

Comparative Example 3

The method of Comparative Example 1 was followed except corn seeds were tested at the highest inoculum rate. In this example, CruiserMaxx® Beans™ Corn was used. CruiserMaxx® Beans is a combination of an insecticide with fungicides, and contains 22.61% Thiamethoxam insecticide, 1.70% Mefenoxam, 1.12% Fludioxonil, Metalaxyl M7S isomers, azoxystrobin fungicides and 74.57% other ingredients. Four CruiserMaxx® Beans-coated corn seeds were placed onto the spore lawn of *C. rosea* 88-710 and ACM941 immediately after the PDA plates were inoculated with the spores. There were 3 replicate plates for each treatment.

Figure 9:
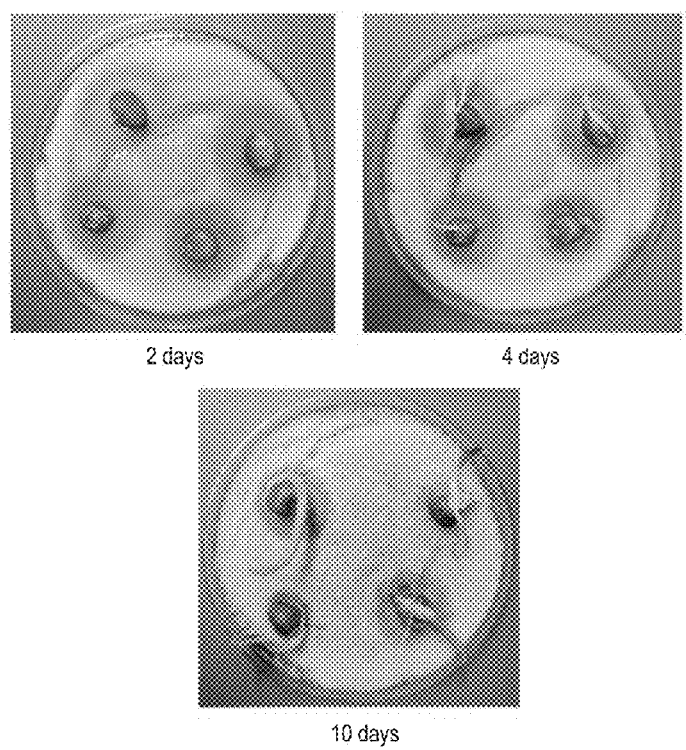
Figure 10:
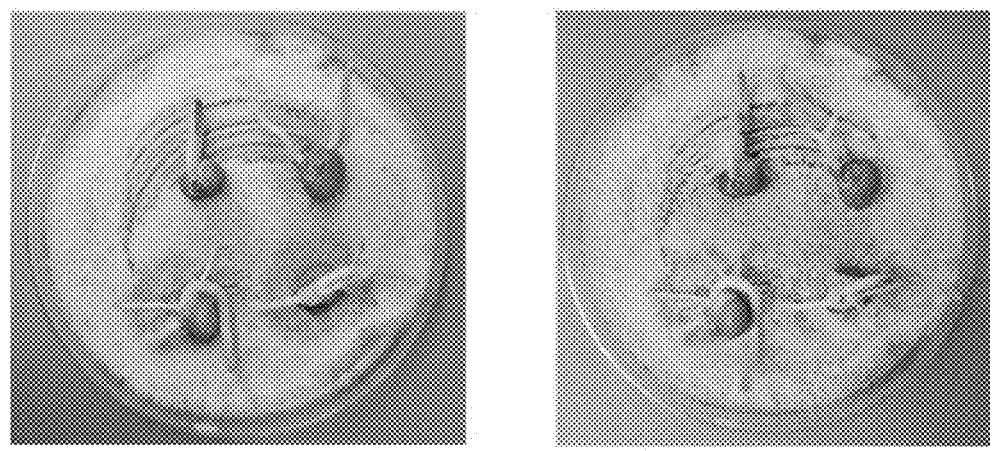

FIGS. 9 and 10 documents the results. FIG. 9 documents the CruiserMaxx® Beans-coated corn seeds on the fresh spore lawn of *C. rosea* 88-710. FIG. 10 documents the CruiserMaxx® Beans-coated corn seeds on the fresh spore lawn of *C. rosea* ACM941.

Example 4

Figure 11:
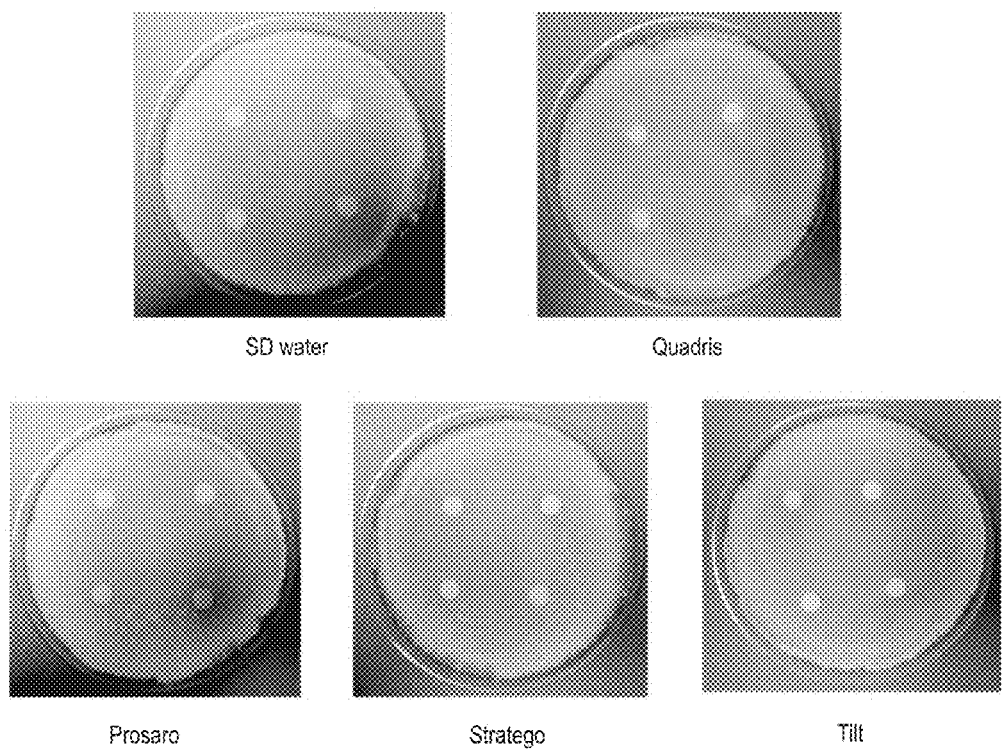

The method of Example 2 was followed, except different fungicides were tested. The results are shown in FIG. 11. FIG. 11 documents that the tested fungicides had little or no effect on growth and sporulation of *C. rosea* 88-710 when the fungicide-treated disks were applied to a lawn of established mycelium.

Comparative Example 5

Figure 12:
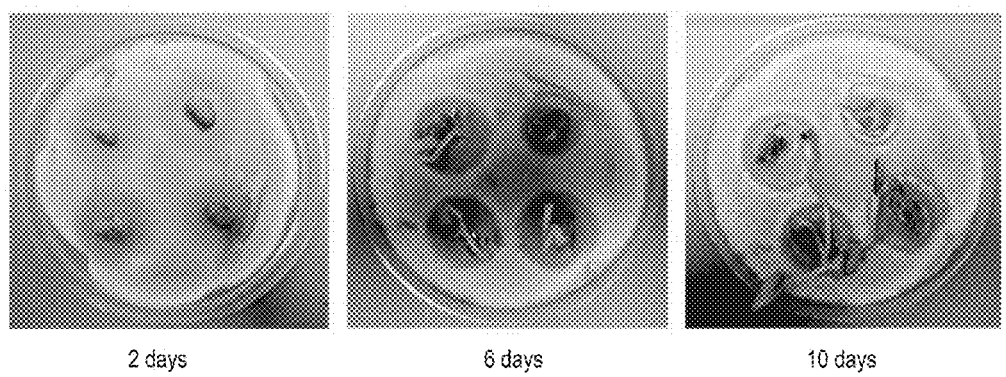

Soybean seeds were treated with a fungicide (Cruiser-Maxx® Beans, a combination insecticide and fungicide, containing Thiamethoxam (CAS No 153719 23 4) 22.61%; Mefenoxam (*CAS No 70630 17 0 and CAS No 69516 34 3) 1.70%, and Fludioxonil (CAS No 31341 86-1) 1.12%) and were then applied to a PDA plate of fresh spore lawn of *C. rosea* 88-710. The results are documented in FIG. 12.

Example 6

Figure 13:
Figure 13:
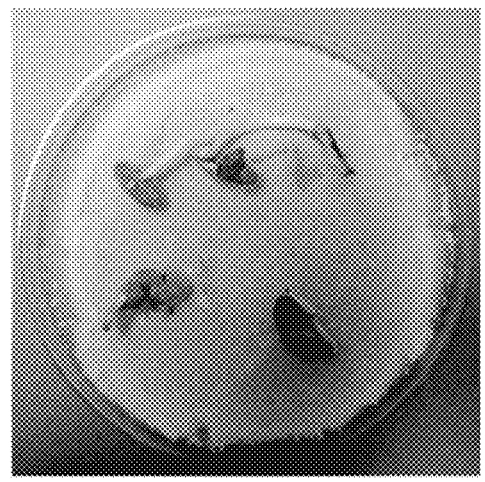

Soybean seeds were treated with a fungicide (Cruiser-Maxx® Beans), and then were applied to a PDA plate of an established 48 hour old spore lawn of *C. rosea* 88-710. The results are documented in FIG. 13, which shows that the tested fungicide have little or no effect on *C. rosea* 88-710 when the fungicide coated soybean seeds applied on the established spore lawn of the fungus.

The observations for disks placed on the agar immediately after application of *C. rosea* spores show that Tilt 250E and Stratego markedly suppressed *C. rosea* germination and growth (35 mm clear zones of inhibition of germination; little growth back over clear zones) (Table 3). Other fungicides produced inhibition zones from 20 to 25 mm in diameter (Table 2). Prosaro inhibited *C. rosea* spore germination, resulting clear zones 1 to 3 mm away from the disks, but did not suppress sporulation of the fungus. Quadris did not inhibit spore germination (no clear zones) but showed some inhibition of mycelial growth and sporulation (FIGS. 4 and 4a).

When fungicide-soaked filter paper disks or seeds were placed onto the established 48-hour mycelia lawn, the tested fungicides had little or no inhibiting effect (FIG. 5).

Example 7

C-Wet was Tested in Seed Treatment

Soybean, wheat, seed corn and turf seed were weighed into ZipLok bags and treated with a conidia suspension of *Clonostachys rosea*. A stock solution for each treatment was prepared using 400 mls of sterile distilled water with *C. rosea* at a cfu count of $1 \times 10^6$th and $2 \times 10^6$th with and without C-Wet adjuvant at 0.3% wt/v. The suspension was filtered through a fine fuel filter within a plastic funnel. Amounts of suspension were calculated to be applied at the equivalent of 10 ml per Kg of seed. The suspension was applied using a spray bottle pump inserted into a 10 ml vial that had a flexible plastic top with a small hole that sealed around the shortened spray pump suction tube. Two sprays were applied onto the seed in the ZipLok bag. The contents within the bag were mixed by rotating the bag. The procedure was repeated twice more to empty the vial. A 10% extra suspension was applied to compensate for loss to the sides of the plastic bag. The bag contents were thoroughly mixed to achieve a relatively uniform distribution over the surface of each seed.

Samples of each seed lot were divided in half after 24 hours and the one portion air dried. The remainder was kept sealed in the plastic bag until a portion was either planted or sent for analysis of colonization.

The Treatments are identified in the following Table 4:

TABLE 4

| Treatment # | *Clonostachys* spore conc.+ | C-Wet | Dried (hours) |
|---|---|---|---|
| 1 | 0 | no | 0* (control) |
| 2 | 0 | no | 24 (control) |
| 3 | $1 \times 10^6$ | no | 0* |
| 4 | $1 \times 10^6$ | no | 24 |
| 5 | $1 \times 10^6$ | yes | 0* |
| 6 | $1 \times 10^6$ | yes | 24 |
| 7 | $2 \times 10^6$ | no | 0* |
| 8 | $2 \times 10^6$ | no | 24 |
| 9 | $2 \times 10^6$ | yes | 0* |
| 10 | $2 \times 10^6$ | yes | 24 |

+conidia/mL water
*Kept very slightly moist in Ziploc bag.

All treatments were applied to wheat and soybean seeds. Seed Corn seeds (flint) and turf-grass seeds received treatments 1, 7, and 9 (labelled as 1, 2 and 3). A sample of each treatment of seeds were analyzed to determine colonization.

Samples of the various crop seeds were planted in a greenhouse. Seeds were planted in shallow trays using a Fafard fine seedling topping mixture (10 seed corn and soy, 15 wheat and 30 turf mixture). The same seedling topping mixture was also used to cover seeds. The plastic trays held 16 rows of treated seed each; 8 rows of non-dried and 8 rows of air dried seed.

Photographs of growth were taken to determine the influence of C. rosea treatment on plant height and root length. The trays containing the various crop plants were cut and plated to measure colonization.

Figure 14:
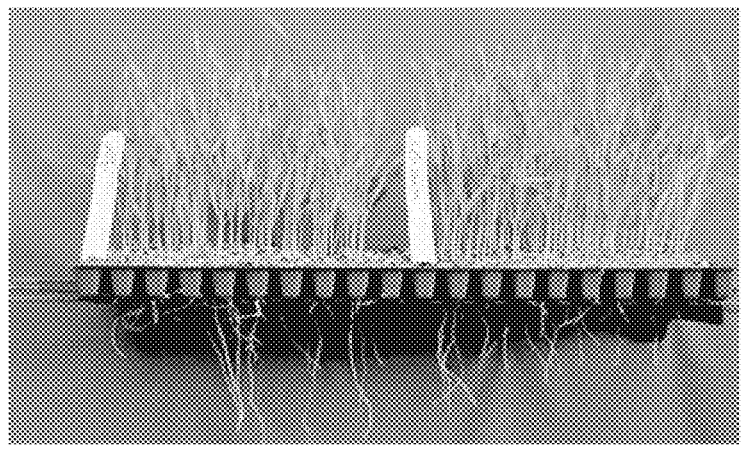

FIG. 14 shows wheat seeds sprayed with 10 ml water/Kg of wheat seed, without any inoculation, and maintained in a plastic bag. Half the seeds were air dried after 24 hours and placed into a second plastic bag. The similarity of root and shoot development may be noted in the image.

Figure 15:
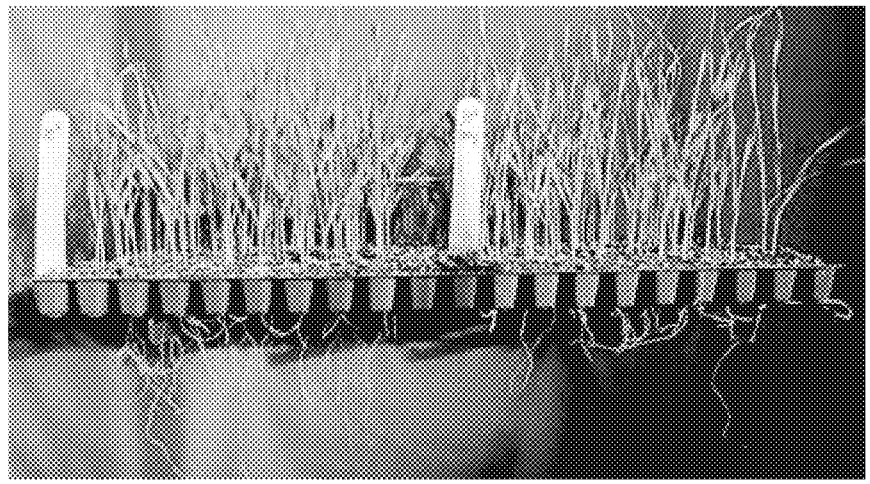

FIG. 15 shows wheat seeds sprayed with 10 ml of Clonostachys rosea suspension (1×10$^6$ colony forming units ["cfu"])/Kg of wheat seed, without C-Wet, and maintained in a plastic bag. Half the seeds were air dried after 24 hours and placed into a second plastic bag. In the Figure, the plants on the left side are from undried seeds, and the plants on the right side are from dried seeds. The shift of root and shoot development may be noted in the image.

Figure 16:
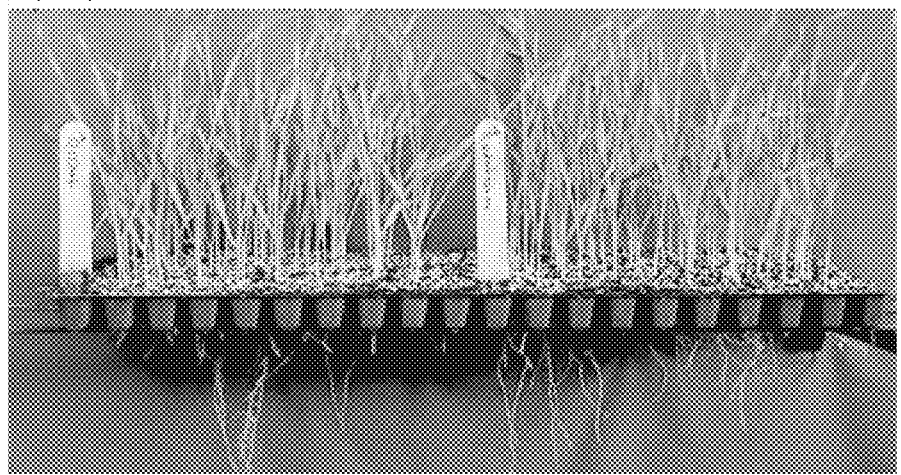

FIG. 16 shows wheat seeds sprayed with 10 ml of Clonostachys rosea suspension (1×10$^6$ cfu/Kg of wheat seed, with C-Wet adjuvant, and maintained in a plastic bag. Half the seeds were air dried after 24 hours and placed into a second plastic bag. In the Figure, the plants on the left side are from undried seeds, and the plants on the right side are from dried seeds. The experiment indicates that Clonostachys rosea had similar inoculation in both the wet and dried seeds, which indicates a rapid uptake of Clonostachys rosea when supplemented with C-Wet.

Figure 17:
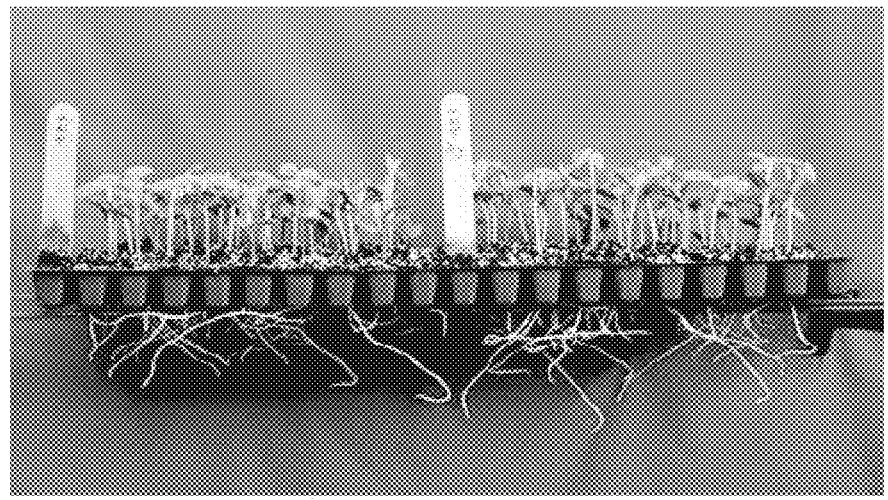
Figure 18:
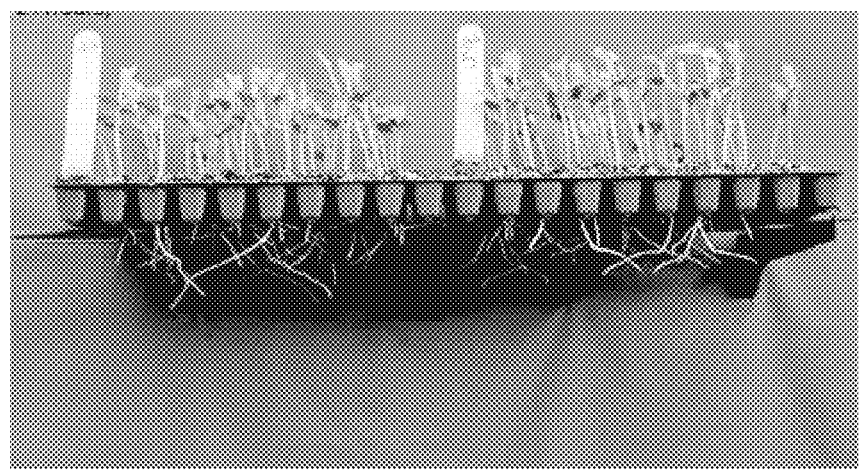

FIGS. 17, 18 and 19 are the results of the tests with soybean seeds, and the descriptions follow those of FIGS. 14-16, respectively. FIG. 17 shows similar root and shoot development. FIG. 18 show a root:shoot shift with soybean seeds treated with Clonostachys rosea without adjuvant. FIG. 19 shows that seeds treated with Clonostachys rosea in combination with C-Wet show similar development in case of both wet and dried seeds, indicating that C-Wet promoted uptake of Clonostachys rosea into soybean seeds.

The experiments did not indicate any significant difference between maintaining seeds at 12-13% moisture and air drying.

Example 8

Effects of C-Wet and UV irradiation on the ability of Clonostachys rosea spores to germinate and establish endophytically in leaves of wheat and corn were tested with the objective of determining the effects of C-Wet employed as an inoculum adjuvant with Clonostachys rosea spores, and of periods of post-inoculation exposure of the inoculum to UV irradiation, on the ability of C. rosea to germinate and establish as an endophyte in wheat and corn leaves.

The tested plants were greenhouse-grown seedlings of wheat (3-leaf stage) and corn (2-3 leaf stage). The wheat was in 4-inch plastic pots and the corn in seedling flats.

The Clonostachys rosea 88-710 strain was prepared with and without C-Wet immediately before the seedlings were inoculated. Four mls of the stock solution was removed with a syringe and placed in a vial with a spray mister.

Foliage of the seedlings was sprayed with inoculum with or without C-Wet. The mist sprayer was charged with the inoculum by gently depressing the spray trigger. The seedlings were placed approximately 20 cm from the sprayer and the trigger rapidly squeezed twice to aspirate all of the inoculum mixture onto the seedling foliage. All seedlings were inoculated within 15 minutes. The spray mister and vial were triple rinsed with bottled water between each application to the seedlings. All of the treatments with the inoculum alone were applied prior to the inoculum with the C-Wet.

The inoculated seedlings were immediately positioned beneath a UV "black lamp" such that the tops of the leaves were 25-50 cm from the light tubes. (Lamp unit: Blak-Ray lamp model XX-15; 115 v, 60 hz 0.75 amp; UVP, San Gabriel, Calif. 91778. Light tubes: GE, Nela Park, Cleveland Ohio 44112; 15 Watt black light F15 T8/BLB "psychodelic light". Two 15 inch light tubes) (Note: The inverse square law states that the light intensity is inversely proportional to the square of the distance from the lamp.)

Treated plants were removed from beneath the lamp after the following periods of UV exposure: 0 h, 1.5 h, 3.0 h, 6.0 h, 9.0 h, 15 h, and 24 h. During these periods the temperature was 20-22° C. and relative humidity 70-80%

At each time of sampling, leaves were cut crosswise into segments and placed on Paraquat-chloramphenicol agar medium (PCA) in Petri dishes. Scissors used for cutting segments were wiped with a tissue wetted with 95% EtOH followed by a dry tissue between each cut. Each segment was positioned in close contact with the PCA to facilitate absorption of the Paraquat and thus accelerate leaf senescence. The rationale for plating on PCA is that C. rosea establishes symptomlessly within leaves and other plant tissues as beneficial endophyte, and sporulates on the tissues only after the tissues begin to senesce. Observation of sporulation is an indirect means to determine endophytic establishment and viability of C. rosea in the tissues. Paraquat accelerates natural senescence and browning of tissues and thereby allows C. rosea to sporulate relatively quickly, often within 8-9 days, and thus facilitates the assessment of endophytic establishment of the fungus. Chloramphenicol is included as a broad spectrum antibacterial antibiotic.

For sampling the wheat, two leaves were cut from two plants in each of 3 pots of each treatment and cut into segments 10-14 mm long. A total of 22 to 30 segments per treatment (i.e. C. rosea, only; and C. rosea plus C-Wet) were placed on PCA in two Petri dishes.

For sampling the corn, all leaves of one seedling from the Cr only and Cr+C-Wet treatments were cut into pieces approximately 8 mm long and positioned on PCA in two Petri plates.

Petri plates with plated leaf segments were placed in translucent plastic boxes. The lids of the boxes were closed, and all boxes were kept on a lab cart at 21-24° C. in dim indoor light during daytime.

The plated leaf segments were examined daily for sporulation of C. rosea. All segments were assessed for sporulation of Clonostachys on DAY 6. Estimation of sporulation is an indirect means for estimating the levels of endophytic establishment of C. rosea in plant tissues.

Sporulation rating scale: Observed sporulation was rated on a scale of 0-10 in which 0=no sporulation, 1=1-10% of leaf area with sporulation, 2=11-20% of leaf area with sporulation . . . 10=90-100% with sporulation. The rating scale approximates a % scale.

TABLE 5

Mean sporulation ratings.

| | Sporulation ratings (%)* | | | | | |
|---|---|---|---|---|---|---|
| | Wheat | | | Corn | | |
| UV exposure period (h) | C.r. | C.r. + C-Wet | % ↑ | C.r. | C.r. + C-Wet | % ↑ |
| 0.0 | 40.4 | 91.7 | 227% | 45.0 | 89.2 | 198% |
| 1.5 | 44.0 | 77.2 | 176% | 36.2 | 79.2 | 219% |
| 3.0 | 40.9 | 71.2 | 174% | 42.5 | 82.5 | 194% |
| 6.0 | 32.2 | 78.2 | 243% | 42.3 | 70.1 | 166% |
| 9.0 | 29.7 | 70.9 | 239% | 36.2 | 72.5 | 200% |
| 15.0 | 17.3 | 45.7 | 264% | 20.0 | 52.5 | 263% |
| 24.0 | 10.0 | 37.4 | 374% | 20.6 | 53.3 | 259% |

*These values closely approximate % values, but strictly speaking all are marginally exaggerated because the end points rather than the mid points for each scale increment were used (e.g. 3.0 instead of 2.6)
% ↑ Percent increase in estimated % area of sporulation by *C. rosea* on leaf segments associated with the use of C-Wet in the inoculum.

TABLE 6

Mean *C. rosea* sporulation rates ± standard error for leaf segments of wheat seedlings.

| UV exposure | Sporulation ratings (%) | |
|---|---|---|
| period (h) | C.r only | C.r + C-Wet |
| 0.0 | 40.4 ± 4.42 AB b | 87.4 ± 5.31 A a |
| 1.5 | 43.2 ± 5.35 A b | 77.2 ± 3.91 AB a |
| 3.0 | 40.9 ± 4.53 AB b | 71.2 ± 4.63 B a |
| 6.0 | 32.2 ± 3.50 AB b | 78.2 ± 4.25 AB a |
| 9.0 | 29.7 ± 3.63 B b | 70.9 ± 6.51 B a |
| 15.0 | 17.3 ± 2.58 C b | 43.7 ± 4.49 C a |
| 24.0 | 10.0 ± 2.09 C b | 37.4 ± 5.31 C a |

Note:
Values within the column with the different upper case letters diff significantly (p ≤ 0.05).
Values within the row with the different lower case letters differ significantly (p ≤ 0.05).

TABLE 7

Mean *C. rosea* sporulation rates ± standard error for leaf segments of corn seedlings.

| UV exposure | Sporulation ratings (%) | |
|---|---|---|
| period (h) | C.r only | C.r + C-Wet |
| 0.0 | 45.0 ± 6.71 A b | 89.2 ± 3.79 A a |
| 1.5 | 36.2 ± 5.94 A b | 79.2 ± 5.43 AB a |
| 3.0 | 42.5 ± 6.64 A b | 81.7 ± 5.88 AB a |
| 6.0 | 42.3 ± 6.90 A b | 70.8 ± 8.57 B a |
| 9.0 | 36.2 ± 5.49 A b | 72.5 ± 5.79 AB a |
| 15.0 | 20.0 ± 5.06 B b | 52.5 ± 4.29 C a |
| 24.0 | 20.5 ± 4.66 B b | 55.0 ± 8.03 BC a |

Note:
Values within the column with the different upper case letters diff significantly (p ≤ 0.05).
Values within the row with the different lower case letters differ significantly (p ≤ 0.05).

The results indicate that C-Wet increased the area of sporulation of *C. rosea* by 174-374% in wheat and by 166-263% in corn (Tables 6-7). This indicates that C-Wet increased endophytic colonization of the leaves by *C. rosea* by these amounts.

Sporulation ratings declined with increase in the period of exposure to UV and reduced humidity mainly when the period exceeded 9 hours, regardless of whether C-Wet was used. (Note that incubation periods on PCA of leaves plated at 15 h and 24 h after inoculation were 15 and 24 h less than the full 6 days for the 0 h samples. Sporulation levels might possibly have increased a bit given this extra time.)

Decline in sporulation ratings when UV exposure periods were increased from 9 h to 24 h were lower when C-Wet was used (for wheat, 66% decline without C-Wet and 47% with C-Wet. For corn, 43% decline without C-Wet and 26% with C-Wet). This suggested that C-Wet provided some protection of the spores against UV or against desiccation or both. This was supported also by the increasing % ↑ values for 9 to 24 h exposure periods (see Table 7).

Exposure periods of up to 6 or 9 hours did not markedly affect the sporulation ratings in any treatment. The exceptionally high ratings for C-Wet-treated wheat and corn at 0 h UV exposure compared to 1.5 h exposure (but not in the absence of C-Wet) was maybe related to spreading and subsequent drying of the C-Wet in sites such as leaf edges (C-Wet seemed to promote sporulation on uncut leaf edges).

There is some possibility that factors other than the treatment variables could potentially have affected spore germination and endophytic establishment of *Clonostachys rosea* and thus sporulation of the fungus on the leaves. These factors, which are typical of biological variability and inherent testing limitations, include the uniformity of spray application; angle and distance of leaves with respect to sprayer and UV lamp; contact of the leaf segment with the PCA (mostly good); other fungi present (the plated leaf segments were almost entirely free from visible growth or sporulation of other fungi; about 7-10 segments with visible sporulation and mycelium of *Penicillium* and/or *Fusarium* were not used for estimating sporulation of *Clonostachys rosea*); and drying of leaves for different periods following spray treatment and before plating of the segments.

Example 9

Seeds of Soybean, Wheat, Corn and Turf-grass mixture were inoculated in the Fall with and without C-Wet as described in the prior examples. The seeds were then stored in a garage at or just above freezing. A fungicide, CruiserMaxx® Beans, was applied about April at 6.6 ml/Kg of seed (10% increase for loss to bag).

The results were that germination incidence of wheat, corn, and soybean seeds that were treated with *Clonostachys rosea* with or without C-Wet, or untreated, and stored over winter, was >98% in all instances. Similar high germination was also obtained in all instances when seeds of these treatments were also treated with the fungicide CruiserMaxx® Beans.

Estimated (detected) incidence values for *Clonostachys rosea* on treated seeds that were stored over winter and not treated with CruiserMaxx® Beans were as follows:
  WHEAT: 40-50%
  CORN: 100%
  SOYBEAN: 70-80%
  TURF-GRASS MIXTURE: >90%

Estimated (detected) incidence values for *Clonostachys rosea* on treated seeds that were stored over winter and treated with CruiserMaxx® Beans were as follows:
  WHEAT: >90%
  CORN: 100%
  SOYBEAN: 70-80%

*Clonostachys rosea* markedly suppressed principal "storage molds" (*Aspergillus* and *Penicillium*) on corn seeds and turf-grass seeds (>92% suppression in the latter). *Paecilomyces, Alternaria* and a few other fungi.

The influence of C-Wet adjuvant on colonization of *Clonostachys rosea* treated seeds was not evident six months after initial application. The results suggest that the mycelium of *Clonostachys* strains will reach an optimum colonization level within the seed and this relationship is truly symbiotic as there was no alteration in the germination of the seeds tested. Fungicide tolerance was excellent as indicated by previous work with established mycelium. Bin run wheat seed showed improved germination when treated with Cruise Maxx.

Example 10

CruiserMaxx® Beans treated seed corn was placed on mature *C. rosea* ACM941 mycelium (48 hours old). FIG. 20 shows that there was no effect of the fungicide on mycelium growth 4 days (FIG. 20*a*) and 10 days (FIG. 20*b*) later.

Figure 21A:
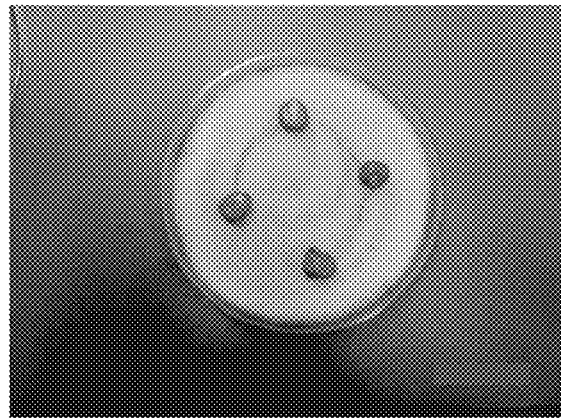
Figure 21B:
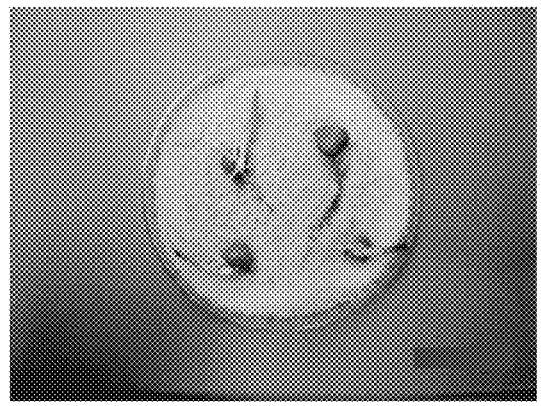

CruiserMaxx® Beans treated seed corn was placed on mature *C. rosea* 88-710 mycelium (48 hours old). FIG. 21 shows that there was little, if any effect of the fungicide on mycelium growth 4 days (FIG. 21*a*) and 10 days (FIG. 21*b*) later.

Although the subject matter has been described in language specific to structural features and/or methodological acts, it is to be understood that the subject matter defined in the appended claims is not necessarily limited to the specific features or acts described above.

Example 11

The effects of C-Wet and CruiserMaxx® Beans on *Clonostachys*, pathogens and molds was tested on *Clonostachys* seed treatments of soybean, wheat, and corn seed following winter storage.

The CR-seeds were inoculated with 88-710 or with 88-710 and C-Wet as shown in Example 7. Some of the seeds were treated with CruiserMaxx® Beans. The fungicide was applied six months after inoculation with 88-710. The test was conducted six months after the date of the CruiserMaxx® Beans application. The treated seeds were plated on Paraquat-chloramphenicol agar medium in Petri dishes on (5 Petri dishes each with 10 seeds for soybean and corn, and 5-dishes each with 15 seeds for wheat). The Petri dishes and seeds were kept in clear plastic boxes at 21-26° C. (mainly 23-25° C.). The seeds were examined microscopically for seed germination and for fungal growth and sporulation after 3 days of incubation and daily thereafter until day 8, with a final check on day 10.

The seed treatments are shown in Table 8:

TABLE 8

| Treatment # | Code | Spores/mL *Clonostachys* |
|---|---|---|
| 1 | UT Check | 0 |
| 2 | CruiserMaxx ® Beans | 0 |
| 3 | 88-710 + C-Wet | $2 \times 10^6$ |
| 4 | 88-710 + CruiserMaxx ® Beans | $2 \times 10^6$ |
| 5 | 88-710 + C-Wet + CruiserMaxx ® Beans | $2 \times 10^6$ |

The effects of the seed treatments on seed germination, the presence of storage molds (*Aspergillus/Penicillium* group) and molds with substantial aerial mycelium are shown in Table 9. The molds were observed on day 4.

TABLE 9

| | | Germination % | | | | | Molds day 4 (0-10)+ | |
|---|---|---|---|---|---|---|---|---|
| | | | | | | | *Asp.* | |
| Crop | Treatment | Day 3 | Day 4 | Day 5 | Day 6 | Day 7 | *Peni* | A-M |
| Soybean | UT check | 4 | 20 | 82 | 82 | 82 | 2/90% | 2 |
| | CruiserMaxx ® Beans | 0 | 4 | 10 | 16 | 16 | 1/20% | 0 |
| | 88-710 + C-Wet | 22 | 72 | 92 | 92 | 92 | 2/85% | 0 |
| | 88-710 + CruiserMaxx ® Beans | 0 | 0 | 0 | 0 | 0 | 2/30% | 2 |
| | 88-710 + C-Wet + CruiserMaxx ® Beans | 0 | 28 | 42 | 56 | 56 | 2/25% | 0 |
| Wheat | UT check | 96.0 | 96.0 | 97.3 | 97.3 | | 1/20% | 0 |
| | CruiserMaxx ® Beans | 25.3 | 42.7 | 42.7 | 42.7 | | 1/5% | 2 |
| | 88-710 + C-Wet | 96.0 | 96.0 | 96.0 | 96.0 | | 1/15% | 1 |
| | 88-710 + CruiserMaxx ® Beans | 26.7 | 37.3 | 37.3 | 37.6 | | 1/25% | 1 |
| | 88-710 + C-Wet + CruiserMaxx ® Beans | 57.3 | 77.3 | 77.3 | 77.3 | | 1/10% | 1 |
| Corn | UT check | 22 | 86 | 97.3 | | | 1/90% | 1 |
| | CruiserMaxx ® Beans | 0 | 0 | 0 | | | ND* | 9 |
| | 88-710 + C-Wet | 26 | 86 | 90.0 | | | 1/90% | 1 |
| | 88-710 + CruiserMaxx ® Beans | 0 | 0 | 0 | | | ND* | 10 |
| | 88-710 + C-Wet + CruiserMaxx ® Beans | 0 | 0 | 0 | | | ND* | 8 |

The +*Aspergillus* and *Penicillium* were grouped together and rated for density on the seeds (scale of 0-10) and % coverage of seeds at this density. "A-M" is the rating of aerial mycelium on the seed and/or fluffy mycelium spreading out from the seed. "ND" means that no results were obtained because obscured by mycelium of other fungi.

As reflected in the above Table 9, the following observations may be made of the germination results:

(i) CruiserMaxx® Beans delayed and partially blocked germination of soybeans and wheat, and completely blocked germination of the corn seed.

(ii) Germination of soybean seeds treated with 88-710+C-Wet+CruiserMaxx® Beans was faster and greater than the germination of CruiserMaxx® Beans alone. The percent germination on days 6 and 7 was about three times greater than with CruiserMaxx® Beans alone. It is unclear why no seeds treated with 88-710+CruiserMaxx® Beans germinated.

(iii) The germination for wheat seeds treated with CruiserMaxx® Beans or with 88-710+CruiserMaxx® Beans was similar (maximum around 40%). However, treatment with 88-710+C-Wet+CruiserMaxx® Beans resulted in 77% germination. Thus it appears that the C-Wet partially counteracted the effects of CruiserMaxx® Beans. Roots growing from seeds treated with CruiserMaxx® Beans were generally stubby and considerable callus-like growth developed close to the seeds. These effects of CruiserMaxx® Beans were much less pronounced in the presence of 88-710+C-Wet (i.e. 88-710+C-Wet+CruiserMaxx® Beans).

As further reflected in the above Table 9, the observations below may be made of the mold results. For assessments, fungal growth on the seeds was categorized as storage molds (i.e. *Aspergillus* plus *Penicillium* or *Asp. Peni*), which generally sporulated close to the seed surface, and other fungi which generally produced a lot of aerial mycelium with or without spores (A-M group) (Table 9).

(iv) Morphologically diverse forms of *Aspergillus* and *Penicillium* grew and sporulated on the soybean seeds. At day 4, the density of these fungi on the seeds was rated as light (1-2). At that time the proportion of seed surface with these fungi was high (near 90%) in the untreated controls and in the 88-710+C-Wet treatment but much lower (20-30%) in all treatments with CruiserMaxx® Beans. Thus CruiserMaxx® Beans reduced growth and sporulation of these storage molds. The density of *Aspergillus* plus *Penicillium* on seeds of the untreated controls and 88-710+C-Wet treatment increased during days 5-8. In seeds treated with CruiserMaxx® Beans (alone or in combinations) growth of these and other fungi was generally sparse.

(v) *Aspergillus* and *Penicillium* were relatively sparse (rating of 10) on wheat seeds of all treatments and the percent coverage of the seeds was low especially in the CruiserMaxx® Beans and 88-710+C-Wet+CruiserMaxx® Beans treatments.

(vi) *Aspergillus* and *Penicillium* were sparse (rating 1) over most (90%) of the corn seed surface in treatments where no CruiserMaxx® Beans was applied (i.e. the controls and 88-710+C-Wet). Corn seed treated with CruiserMaxx® Beans were quickly covered by aerial mycelium of other fungi which obscured *Aspergillus* and *Penicillium*.

(vii) Many fungal colonies on seeds treated with CruiserMaxx (alone or in combination) showed abnormal growth, as might be expected.

(viii) *Fusarium* spp. and other fungi with aerial mycelium grew over a few soybean and wheat seeds.

(ix) In corn, *Fusarium* spp, including *F. verticillioides* (=*F. moniliforme*), and other unidentified fungi with aerial mycelium grew rapidly and abundantly on and around seeds treated with CruiserMaxx® Beans (alone or in combination), none of which germinated. Little aerial growth developed on the untreated controls or on the 88-710+C-Wet treatment which germinated well. Thus the CruiserMaxx® Beans apparently predisposed the seeds to mold growth perhaps because it initially stressed and finally killed the seeds.

As further reflected in the above Table 9, the following observations may be made regarding *Clonostachys rosea:*

(x) Soybean and wheat: Sporulation of *Clonostachys rosea* was not found on soybean or wheat seeds of any treatment (final assessment day 10) for reasons that are unclear.

(xi) Corn: *Clonostachys rosea* was found on seeds inoculated with 88-710 (i.e. 88-710+C-Wet, 88-710+CruiserMaxx® Beans, and 88-710+C-Wet+CruiserMaxx® Beans) but not on non-inoculated seeds (i.e. the untreated checks and CruiserMaxx® Beans). Values for percent seeds with *Clonostachys rosea* were not obtained for practical reasons. *Clonostachys rosea* was first identified on day 5 and was more abundant at day 8. As in earlier findings, *Clonostachys rosea* exhibited tolerance of CruiserMaxx® Beans, and did not seem to be morphologically affected by the fungicide.

(xii) *Clonostachys rosea* was identified based on conidiophore morphology (verticillate form was present) and the size, uniformity and kidney bean shape of the spores. The observations were done with a stereoscopic microscope and on a compound microscope using up to 400× magnification. Conidiophores and spores were observed directly on the seeds and surrounding agar medium. Spores and conidiophores on the medium were observed in part by placing a drop of water on the agar and covering it with a microscope cover glass to avoid fogging of the 40×).

As further reflected in the above Table 9, the following observations may be made regarding germination:

(xiii) The fungicide CruiserMaxx® Beans markedly reduced the % germination of soybean and wheat and blocked germination of the corn. These results are in contrast to other findings in which germination was not reduced.

(xiv) Percent germination of untreated control seeds and seeds treated with 88-710+C-Wet (no CruiserMaxx® Beans) remained high.

(xv) *Clonostachys rosea* remained well established in or on the 88-710 treated corn seeds (with or without CruiserMaxx® Beans); whether there was any reduction in % seeds with *Clonostachys* was not determined.

(xvi) CruiserMaxx® Beans reduced germination of SOYBEANS by 80% when used alone but by only 32% when used in combination with 88-710 and C-Wet (i.e. 88-710+C-Wet+CruiserMaxx® Beans). Thus 88-710+C-Wet ameliorated the impact of CruiserMaxx® Beans even though 88-710 was not recovered from the seeds at this time of assessment.

(xvii) Similarly CruiserMaxx® Beans reduced germination of the WHEAT by 56% when used alone compared to 25% when used in combination with 88-710+C-Wet. Again, 88-710 was not recovered from the seeds at this time of assessment.

(xviii) Taken in perspective with the results shown in Example 9 that showed high incidence of *C. rosea* 88-710 in the seeds, the data noted in xvii and xviii suggest that there was a residual physiological effect of earlier *Clonostachys rosea* colonization of the seeds in which resistance of the seeds to stress associated with CruiserMaxx® Beans treatment was enhanced.

Example 12

An experiment was conducted to determine the effectiveness of treating wheat seeds with *Clonostachys rosea* 88-710 and *Clonostachys rosea* ACM491, with C-Wet, in reducing incidence of *Fusarium graminearum* and concentration of *Fusarium* Head Blight ("FHB") in the seeds during storage at cool temperature (16-18° C.). Such efficacy could potentially increase the grade of contaminated seeds.

The materials and methods were as follows:

The seed lots comprised *Durum* wheat with "5.8% initial FHB" and *Durum* wheat with "18.2% initial FHB," both sourced from Saskatchewan, Canada.

The Seed treatments:
1 Control 10 mL water/Kg seed
2 ACM-491+C-Wet ver 1 10 mL suspension/Kg seed
3 ACM-491+C-Wet ver 2 10 mL suspension/Kg seed
4 Endofine Express 10 mL suspension/Kg seed Ver 1 and Ver 2 were early and somewhat unstable formulations of *C. rosea* ACM491 plus an adjuvant system. Endofine Express is a powdered formulation of *C. rosea* 88-710 (spore concentration 2×106/mL) plus C-Wet at 5% wt/wt.

Eight samples (i.e., the two seed lots×the four treatments; 250 g treated seeds of each) were treated with Vers ½ and Endofine Express as indicated. The seeds of each treatment were plated on Paraquat-chloramphenicol agar medium on March 9 (25 seeds in each of 5 Petri plates per treatment i.e. 125 seeds per treatment). Before plating, small quantities of the seeds (15-25) were scooped from the bag with a mini lab scoop to minimize possible bias in selecting badly affected seeds (tombstones, shrivelled etc) or seeds that appeared "good." All seed handling tools were sterilized with EtOH between samples. The plated seeds (i.e. Petri dishes in clear plastic boxes) were incubated at 22-24° C. with some low intensity artificial and natural light each day.

The seeds were examined on a stereoscopic microscope at 3 and 4 days after plating, and photos were taken of representative plates on day 5. After examining seeds of each treatment a decision was made to estimate/count the following four variables:

1 Number of seeds with mycelial colonies of *Fusarium* (these were well developed colonies with aerial mycelium; minor mycelia growth not included; identity confirmed for samples of each treatment by observing morphology on a compound microscope; a few were sub-cultured onto PDA streptomycin agar medium)

2 Number of seeds with mycelia colonies that ALSO showed reddish pigment (typical of *Fusarium*) when viewed from beneath the plates.

3 Number of seeds with *Penicillium/Aspergillus*. Only seeds with obvious colonies of these were counted. Data approximate. Values shifted a lot over time.

4 Number of germinated seeds.

Variables 1-4 were assessed on day 4 after plating.

Seeds were examined for *C. rosea* on days 6 and 7. Other fungi were very infrequent (included *Alternaria*; and maybe two mucoraceous fungi) and were not assessed numerically.

The results are shown in Table 10.

TABLE 10

| % SEEDS | | | | | | |
|---|---|---|---|---|---|---|
| | | *Fusarium* | | | | |
| FHB % | Treatment | Colonies | Red P. | Treatment Effects (%)* | *Penic. Asperg.* | Seed Germin. |
| 5.8% | Control | 61.6 | (23.2) | — (—) | 26.4 | 58.4 |
| | Ver 1 | 39.2 | (16.8) | −36.4 (−27.5) | 13.6 | 72.8 |
| | Ver 2 | 45.6 | (19.2) | −26.0 (−17.2) | 4.0 | 64.8 |
| | Endofine Exp. | 42.4 | (20.8) | −31.1 (−10.3) | 8.8 | 59.2 |

TABLE 10-continued

| % SEEDS | | | | | | |
|---|---|---|---|---|---|---|
| | | *Fusarium* | | | | |
| FHB % | Treatment | Colonies | Red P. | Treatment Effects (%)* | *Penic. Asperg.* | Seed Germin. |
| 18.2% | Control | 69.6 | (32.8) | — (—) | 24.8 | 46.4 |
| | Ver 1 | 43.2 | (26.4) | −37.9 (−19.5) | 12.8 | 52.8 |
| | Ver 2 | 60.0 | (36.8) | −14.0 (+12.2) | 8.0 | 41.6 |
| | Endofine Exp. | 45.6 | (30.4) | −35.4 (−7.3) | 22.4 | 42.4 |

In the above Table, the percent values for *Fusarium* are based on total seeds with mycelial colonies of *Fusarium* and in parentheses % values for colonies that ALSO showed reddish pigment (Red P.). Treatment effects in the first two columns expressed as % of the controls. e.g., for the 5.8% FHB tests, Ver 1 decreased incidence of *Fusarium* colonies by 36.4% and seeds with red pigment by 27.5%.

As reflected in the above Table, the observations below may be made of the results:

(i) Ver 1, Ver 2 and Endofine Express each suppressed *Fusarium* on the wheat seeds (based on the methods employed to quantify the pathogen).

(ii) Overall the results for Ver F1 and Endofine Express were closely similar and superior to Ver 2.

(iii) The data indicate that (compared to the controls) *Clonostachys rosea* ACM941 and 88-710 in the three products suppressed the ability of *Fusarium* to (A) grow out from the seeds to form aerial mycelium and (B) grow intensively on or near the seeds so as to produce red pigment. These findings can be interpreted to indicate that *Clonostachys rosea* strains actively suppressed *Fusarium* on/in the seeds during storage (i.e. between the time the seeds were treated and when plated on PCA), and during subsequent incubation under the moist conditions on the PCA.

(iv) The frequencies of seeds with red pigment increased during the days following the assessments of day 4. This presumably means that *Fusarium* continued growing in the PCA environment, even from areas of seed colonization by the pathogen that were very limited at the time of plating.

(v) *Clonostachys rosea* suppressed sporulation of the *Penicillium/Aspergillus* group (as observed in the past).

(vi) The percentage germination of the seeds in these seed lots was variable. The more defective the seeds the greater were the *Fusarium* infestation generally.

The establishment of *Clonostachys rosea* in the wheat seeds was then evaluated. The plated wheat seeds were examined for sporulation of *Clonostachys rosea* on day 7 after plating using a stereomicroscope. Sporulation was most easily seen on seeds or portions of seeds with little or no mycelium of *Fusarium*. However in all treatments there was considerable variability in incidence and density of *Clonostachys* sporulation on the seeds, with density varying from very light to extremely dense.

The estimated sporulation of *Clonostachys* on the wheat seeds at 7 days after plating on PCA is shown in Table 11:

TABLE 11

| FHB % | Treatment | *Clonostachys* sporulation Index (0-5)* |
|---|---|---|
| 5.8 | Control | 0 |
|  | Ver 1 | 4 |
|  | Ver 2 | 5 |
|  | Endofine Express | 5 |
| 18.2 | Control | 0 |
|  | Ver 1 | 3 |
|  | Ver 2 | 2 |
|  | Endofine Express | 3 |

As reflected in the above Table, the observations below may be made of the results:

(i) Sporulation was very heavy on some seeds but sparse on others. The likely cause is the differential ability to establish on seeds with differing levels of disease or senescence.

(ii) Substantially less sporulation was found on the seeds with 18.2% FHB compared to 5.8% FHB. The reason is unclear.

Example 13

Experiments were conducted to determine the compatibility of a spray application of fungicides Elevate® (a 50 DWG of active ingredient Fenhexamid (CAS Number: 126833-17-8), Scala® SC fungicide (Pyrimethanil: 4,6-dimethyl-N-phenyl-2-pyrimidinamine), Rovral (Iprodione: 3-[3,5-dichlorophenyl]-N-[1-methylethyl]-2,4-dioxo-1-imidazolidinecarboxamide), Prosaro (mixture of active ingredients: Prothioconazole, 2-[2-(1-Chlorocyclopropyl)-3-(2-chlorophenyl)-2-hydroxypropyl]-1,2-dihydro-3H-1,2,4-triazole-3-thione, 19.0%; and Tebuconazole, alpha-[2-(4-chlorophenyl)ethyl]-alpha-(1,1-dimethylethyl)-1H-1,2,4-triazole-1-ethanol, 19.0%); and Quadris® (Azoxystrobin: methyl (E)-2-{2-[6-(2-cyanophenoxy)pyrimidin-4-yloxy]phenyl}-3-methoxyacrylate) with preceding applications of the biocontrol products EndoFine and EndoFine Express. Endofine is *C. rosea* 88-710 (spore concentration $2 \times 10^6$/mL). Endofine Express is a powdered formulation of *C. rosea* 88-710 (spore concentration $2 \times 10^6$/mL) plus C-Wet at 5% wt/wt.

A test under vineyard conditions was conducted. For each treatment there were 3 replicate plots (rows of grape vines).

Leaves were sampled in all plots on the morning of 15 Aug. 2014, two days after the final fungicide applications (i.e. 8 days after the Endofine treatments were applied). For each treatment nine leaves were taken at random from each side of the grape row (i.e. samples 1 and 2 of each plot). The two groups of nine leaves were placed in separate Ziploc bags in a cooler with freezer packs and delivered for laboratory analysis.

Twenty 15 mm diameter disks were cut from each sample of 9 leaves (i.e. two disks from each leaf plus two additional disks from random leaves). Disks were cut from random sites on the leaves using a sterilized cork borer and placed on the PCA in Petri dishes on Aug. 16 and 17, 2014. For each treatment 10 disks were positioned 6-9 mm apart in each of two Petri dishes for a total of 20 disks per treatment (photos taken). A total of 1920 disks were thus plated in 192 Petri dishes. The Petri dishes were incubated in translucent plastic boxes in low intensity daylight at 20-22° C. The disks were examined daily for initial sporulation beginning at day 7 after plating. Disks were observed on a stereoscopic microscope with some identity confirmations made at higher magnifications on a compound microscope.

The observations are as follows:

(i) *Clonostachys rosea* sporulates mainly as the tissues turn brown (ecologically it is a rapid pioneer colonizer of senescing and dead tissues). Browning among leaf disks was somewhat uneven over time for reasons such as:

(A) Natural physiological diversity among the leaves from which the disks were taken (some leaves were intensely green and take longer to senesce than others that were pale green or yellowish; leaves varied in thickness and probably surface wax thickness).

(B) The rate of uptake of Paraquat from the agar medium into the disks depends on how well the disks have contact with the medium. Contact was limited in some disks by natural disk "waviness" and by leaf veins of varying thickness holding the disks partially above the agar.

(C) *Clonostachys rosea* is identified by recognizing tree-like spore-bearing structures of which there are two kinds i.e. "verticillate conidiophores" and "penicillate conidiophores". The "verticillate conidiophores" tend to appear first and are favoured by higher moisture such as near droplets oozing from dead tissues. The "penicillate conidiophores" are extremely white and usually easy to recognize on a stereoscopic microscope.

(ii) Because of the somewhat irregular senescence and browning among leaf disks, disks of all treatments were assessed twice for *Clonostachys rosea*. In the first assessment (day 9 after plating) disks observed as positive for sporulation were marked (on the bottoms of the Petri plates). In the second assessment (day 12) sporulation on the marked disks was confirmed and any additional disks with sporulation were marked. The total numbers of positive disks were recorded. Care was taken to avoid false positives such as could be caused by growth of *Clonostachys rosea* over time from one disk to another (reassessment at day 12 avoided this). As well *Clonostachys rosea* conidia could be dispersed by mites; these were few (initially one per 15-20 plates) and were easily located and "taken out" with military precision using forceps (moth balls were used in the plastic boxes with the Petri plates only after day 12).

(iii) Growth of downy mildew mycelium (Plasmopara) was frequent and often abundant on the undersides of the leaf disks; tended to break down during 12 days of incubation. As to others: *Botrytis cinerea* (occasional); *Alternaria alternata* (common); *Cladosporium* (not common); *Penicillium* and *Aspergillus* (occasional); *Pestalotia* (not common).

The Endofine results are reflected in Tables 12 and 13, indicating whether *Clonostachys* sporulated on the disk, without quantitative assessment:

| | | Sporulation incidence of *C. rosea* on leaf disks | | | | | |
|---|---|---|---|---|---|---|---|
| | | Fungicide | | (Number/20 disks) | | | |
| Treat. # | *C. rosea* formn. | Name | Day appl.* | Rep. 1 | Rep. 2 | Rep. 3 | Mean | % |
| 1 | Endofine | None | 1 | 6 | 8 | 0 | 4.67 | 23% |
| 2 | | None | 6 | 4 | 8 | 9 | 7.00 | 35% |
| 3 | | Rovral | 1 | 7 | 4 | 2 | 4.33 | 22% |
| 4 | | Rovral | 6 | 4 | 2 | 6 | 4.00 | 20% |
| 5 | | Scala | 1 | 2 | 5 | 3 | 3.33. | 16% |
| 6 | | Scala | 6 | 4 | 5 | 4 | 4.33 | 22% |
| 7 | | Elevate | 1 | 7 | 0 | 4 | 3.66 | 18% |
| 8 | | Elevate | 6 | 4 | 4 | 4 | 4.00 | 20% |

TABLE 13

Sporulation incidence of C. rosea on leaf disks

| Treat. # | C. rosea formn. | Fungicide Name | Day appl.* | Rep. 1 | Rep. 2 | Rep. 3 | Mean | % |
|---|---|---|---|---|---|---|---|---|
| 1 | Endofine | None | 1 | 9 | 8 | 3 | 6.67 | 33% |
| 2 | | None | 6 | 2 | 5 | 8 | 5.00 | 25% |
| 3 | | Rovral | 1 | 5 | 4 | 4 | 4.33 | 22% |
| 4 | | Rovral | 6 | 5 | 6 | 4 | 5.00 | 25% |
| 5 | | Scala | 1 | 3 | 5 | 2 | 3.33 | 17% |
| 6 | | Scala | 6 | 6 | 4 | 4 | 4.67 | 23% |
| 7 | | Elevate | 1 | 8 | 3 | 5 | 5.33 | 27% |
| 8 | | Elevate | 6 | 3 | 2 | 3 | 2.67 | 13% |

The Endofine Express results are reflected in Tables 14 and 15:

TABLE 14

Sporulation incidence of C. rosea on leaf disks

| Treat. # | C. rosea formn. | Fungicide Name | Day appl.* | Rep. 1 | Rep. 2 | Rep. 3 | Mean | % |
|---|---|---|---|---|---|---|---|---|
| 1 | Endofine | None | 1 | 8 | 9 | 9 | 8.66 | 43% |
| 2 | Express | None | 6 | 11 | 11 | 8 | 10.00 | 50% |
| 3 | | Rovral | 1 | 6 | 8 | 7 | 7.00 | 35% |
| 4 | | Rovral | 6 | 12 | 7 | 7 | 8.67 | 43% |
| 5 | | Scala | 1 | 6 | 5 | 9 | 6.66 | 34% |
| 6 | | Scala | 6 | 6 | 4 | 4 | 5.33 | 27% |
| 7 | | Elevate | 1 | 6 | 6 | 6 | 6.00 | 30% |
| 8 | | Elevate | 6 | 12 | 5 | 6 | 7.67 | 38% |

TABLE 15

Sporulation incidence of C. rosea on leaf disks

| Treat. # | C. rosea formn. | Fungicide Name | Day appl.* | Rep. 1 | Rep. 2 | Rep. 3 | Mean | % |
|---|---|---|---|---|---|---|---|---|
| 1 | Endofine | None | 1 | 6 | 9 | 7 | 7.33 | 37% |
| 2 | Express | None | 6 | 7 | 14 | 12 | 11.00 | 55% |
| 3 | | Rovral | 1 | 8 | 7 | 6 | 7.00 | 35% |
| 4 | | Rovral | 6 | 11 | 6 | 8 | 8.33 | 42% |
| 5 | | Scala | 1 | 8 | 4 | 6 | 6.00 | 30% |
| 6 | | Scala | 6 | 6 | 7 | 10 | 7.67 | 38% |
| 7 | | Elevate | 1 | 7 | 2 | 7 | 5.33 | 27% |
| 8 | | Elevate | 6 | 9 | 5 | 10 | 8.00 | 40% |

As reflected in the above Tables, the following observations may be made:

(i) 30-50% of disks with sporulation suggests excellent coverage with EndoFine, especially given that the leaves had a fair amount of physiological variability, and microclimatic factors. Some disks rated as negative may be lightly colonized such that *Clonostachys rosea* will still emerge. Rate of emergence through the epidermis of the centres of disks is slower than from the cut (i.e. wounded) edges.

(ii) Overall average (i.e. for all treatments) for % leaf disks with *Clonostachys* was 1.72 times higher for Endofine Express compared to EndoFine. Value for EndoFine Express/Endofine treatments only (i.e. for day 1 plus 6) is about 1.6 times.

(iii) The amount of sporulation on disks from leaves treated with EndoFine Express appeared higher on average than for EndoFine, although no quantitative measurements were made.

Example 14

Experiments were conducted to determine the effects of a spray program of EndoFine Express on the incidence of *Clonostachys rosea* 88-710, fungal pathogens and other mycoflora in the leaves of sweet cherry and raspberry, and particularly to determine the endophytic establishment of *Clonostachys rosea* in cherry and raspberry foliage when applied in combination with C-Wet (i.e. as the EndoFine Express formulation) in a spray program, and to determine effects of the spray program on disease/pathogen development.

On sweet cherries, the results of the tests were as follows:

(i) Observations of leaf disks at 8 days after plating on PCA showed that, with leaves treated with EndoFine Express, *C. rosea* sporulated on 18 of 32 leaf disks that were plated adaxial side upwards (upper side upwards) or 56% of the disks. This indicated that *Clonostachys rosea* had colonized at least half of the cherry leaf area.

(ii) Areas of disks (including some entire disks) with *C. rosea* sporulation were almost entirely free from sporulation and visible mycelia growth of other fungi. This indicates that *Clonostachys rosea* occupies senescing tissues as a pioneer colonizer and blocks colonization by other fungi (including pathogens).

(iii) *C. rosea* was also observed to be growing on other fungi including *Epicoccum nigrum* and on pycnidia of *Coniothyrium*. This was presumed, but not proven, to be mycoparasitism/hyperparasitism.

(iv) Sporulation of *C. rosea* was also found on disks that were plated abaxial or lower side upwards, but leaf hairs, droplets of moisture and exudates and some mycelium of other fungi confounded any realistic incidence counts (v) No sporulation of *C. rosea* was found on disks from untreated leaves.

(vi) The same kinds of fungi were found on the treated and untreated leaves. The % leaf area collectively occupied by these fungi was significantly less (about 40-50% less) in the treated leaves because of preclusion/exclusion from areas of occupation by *Clonostachys rosea*. It was impractical, however, to estimate areas occupied by specific fungi. With reference to specific fungi:

(A) *Alternaria alternata*. This was abundant (as expected on plant foliage). Some strains are pathogenic to cherries (leaf spots, fruit rot). *Clonostachys rosea* appeared to be growing on (parasitizing) some of the *Alternaria* colonies. *C. rosea* is known to be a good biocontrol agent against various Alternarias.

(B) *Cladosporium* spp. Again, these are abundant on plant foliage.

(C) *Coniothyrium* sp. These have been reported to cause stem cankers and leaf spots in cherries. Pycnidia with exuding dark brown to blackish droplets containing spores were visible on the leaf disks using a stereomicroscope.

(D) *Colletotrichum* sp. From descriptions this was *Colletotrichum acutatum*; this diagnosis was based on the fusiform shape (tapered at both ends) shape of the one-celled spores. This species is not listed on sweet cherries in "Fungi on plants and plant products in the United States" but is extremely destructive in strawberries (anthracnose).

(E) *Fusarium* spp. In general these produced mainly mycelium (on and above the leaf disks) and spores.

(F) *Epicoccum nigrum* was localized on the disks and presumptively parasitized in some areas by *C. rosea*. *Epicoccum* is a common early colonizer of senescing plant foliage.

(G) *Botrytis cinerea*. Only traces were found.

On Raspberries, the results of the tests observed 9 days after plating on PCA (observations were also made at 12 days but the results were essentially the same as at 9 days) were as follows:

(vii) *Clonostachys rosea* sporulated on 12 of 34 disks from leaves treated with EndoFine Express i.e. on 34% of the disks. Given the proportions of the leaf disks with sporulation, this indicated that *Clonostachys rosea* had generally established as an endophyte in about 15-25% of the leaf area of the raspberries. Frequency of sporulation was about the same regardless of which way up the disks were plated (i.e. adaxial or abaxial). Intensity of sporulation on disks rated as positive was judged as being lower than in the cherry disks.

(viii) No fungi were found sporulating on over 60% of the surface area of disks (day 9). Bacteria may have occupied the leaf tissues as they died on the PCA medium, but no bacterial colonies were found on the disks. It was not practical to estimate whether the area occupied by other fungi differed in the disks from treated and untreated raspberries. With reference to specific fungi:

(A) *Alternaria alternata*. This was relatively abundant. *A. alternata* can affect harvested raspberries.

(B) *Cladosporium* sp. Fairly abundant. Early colonizer.

(C) *Pestalotia* sp. This is not listed as a pathogen of raspberry. Found on disks from treated and untreated leaves.

Example 15

Experiments were conducted to determine the tolerance to fungicides at high rates and compatibility of a spray application of Elevate, Scala, Rovral, Prosaro or Quadris fungicides with preceding applications of the biocontrol products EndoFine Express (*Clonostachys rosea* str 88-710) and DONguard (*Clonostachys rosea* str. ACM941) in cherry and raspberry foliage, and particularly to determine the influence of Elevate, Scala, Rovral, Prosaro and Quadris sprays applied to cherry and raspberry foliage on the endophytic development and biological activity of *Clonostachys rosea* strains previously applied to the foliage as EndoFine Express and DONguard formulations.

The CFU count on the two strains were as follows: ACM941 was $2.34 \times 10^8$ and 88-710 was $1.44 \times 10^8$. Therefore the percent colonization should be adjusted upward by multiplying the EndoFine Express count by 1.5.

The results are shown in Tables 16-19:

TABLE 16

Sweet Cherry leaf disks

| Treatment | Fungicide | Plate # | Cr incidence | % disks with Cr |
|---|---|---|---|---|
| DONguard check | None | 1 | 1/12 | 41.7% |
| | | 2 | 8/12 | |
| | | 3 | 4/12 | |
| | | 4 | 7/12 | |
| DONguard | Elevate | 1 | 6/12 | 38.3% |
| | | 2 | 5/12 | |
| | | 3 | 3/12 | |
| | | 4 | 5/12 | |
| | | 5 | 4/12 | |

TABLE 16-continued

Sweet Cherry leaf disks

| Treatment | Fungicide | Plate # | Cr incidence | % disks with Cr |
|---|---|---|---|---|
| DONguard | Prosaro | 1-5 | 1/48 | 2.1% |
| DONguard | Quadris | 1-4 | 0/48 | 0.0% |
| DONguard | Rovral | 1 | 5/12 | 36.7% |
| | | 2 | 5/12 | |
| | | 3 | 2/12 | |
| | | 4 | 5/12 | |
| | | 5 | 5/12 | |
| DONguard | Scala | 1 | 6/12 | 55.0% |
| | | 2 | 7/12 | |
| | | 3 | 8/12 | |
| | | 4 | 6/12 | |
| | | 5 | 6/12 | |

TABLE 17

Sweet Cherry leaf disks

| Treatment | Fungicide | Plate # | Cr incidence | % disks with Cr |
|---|---|---|---|---|
| ENDOFINE EXP. | Elevate | 1 | 2/12 | 18.3% × |
| | | 2 | 2/12 | 1.5 = 27.4% |
| | | 3 | 3/12 | |
| | | 4 | 1/12 | |
| | | 5 | 3/12 | |
| ENDOFINE EXP. | Prosaro | 1-5 | 0/48 | 0.0% |
| ENDOFINE EXP. | Quadris | 1-4 | 0/48 | 0.0% |
| ENDOFINE EXP. | Rovral | 1 | 3/12 | 23.3% × |
| | | 2 | 4/12 | 1.5 = 35.0% |
| | | 3 | 2/12 | |
| | | 4 | 2/12 | |
| | | 5 | 3/12 | |
| ENDOFINE EXP. | Scala | 1 | 4/12 | 26.7% × |
| | | 2 | 3/12 | 1.5 = 40.9% |
| | | 3 | 3/12 | |
| | | 4 | 4/12 | |
| | | 5 | 2/12 | |

TABLE 18

Raspberry leaf discs and half-berries

| | | | Cr incidence | | | |
|---|---|---|---|---|---|---|
| Treatment | Fungicide | Plate # | Disks | % Disks | Berries | % Berries |
| DONguard | Elevate | 1 | 2/10 | 20% | 0/10 | 0.0% |
| | | 2 | 3/10 | | | |
| | | 3 | 1/10 | | | |
| DONguard | Prosaro | 1-3 | 0/36 | 0.0% | 0/10 | 0.0% |
| DONguard | Quadris | 1-3 | 0/36 | 0.0% | 0/10 | 0.0% |
| DONguard | Rovral | 1-3 | 0/36 | 0.0% | 0/10 | 0.0% |
| DONguard | Scala | 1-3 | 0/36 | 0.0% | 2/10 | 20.0% |

TABLE 19

| | | | Cr incidence ( ) means x 1.5% | | | |
|---|---|---|---|---|---|---|
| Treatment | Fungicide | Plate # | Disks | % Disks | Berries | % Berries |
| Endofine Exp. | None | 1 | 5/12 | 33.3% (50.0%) | 0/10 | 0.0% |
| | | 2 | 3/12 | | | |
| Endofine Exp. | Elevate | 1-3 | 0/30 | 0.0% | 0/10 | 0.0% |
| Endofine Exp. | Prosaro | 1-3 | 1/36 | 2.7% (4.1%) | 0/10 | 0.0% |
| Endofine Exp. | Quadris | 1-3 | 0/30 | 0.0% | 0/10 | 0.0% |
| Endofine Exp. | Rovral | 1-3 | 2/30 | 6.6% (9.9%) | 0/10 | 0.0% |
| Endofine Exp. | Scala | 1-3 | 0/36 | 0.0% | 3/10 | 30.0% (45%) |

The following observations may be made:

(i) Discs of Sweet Cherry on plates 1 to 5 were from progressively older leaves; numbers of plates differ slightly because of leaf tissue availability. Good establishment of *Clonostachys rosea* in leaves.

(ii) Elevate, Rovral and Scala did not appear to affect *Clonostachys rosea* establishment (Scala enhanced it?). Sporulation extensive on disks with Elevate.

(iii) Mainly no difference in establishment in younger vs older leaves (i.e. as progress from plate 1 to plate 5) in DONguard plus Elevate, Rovral, or Scala. DONguard check is low in youngest leaf, likely as result of a single application 2 days prior to fungicidal application.

(iv) Prosaro and Quadris essentially inactivated *Clonostachys rosea* in his particular experiment where both sides of the leaf were treated.

(v) Establishment of *Clonostachys* with EndoFine Express in some experiments was about half that for DONguard (Table 16) in leaves treated with Elevate, Rovral or Scala. However, because of low CFUs, Prosaro and Quadris essentially inactivated *Clonostachys rosea* in EndoFine Express.

(vi) Neither DONguard nor EndoFine Express were inactivated by Elevate (fenhexamid), Scala (pyrimethanil) or Rovral (iprodione). Previous results at lower rates have shown tolerance to strobilurin and conazole chemistry.

Many variations of the invention will occur to those skilled in the art. Some variations include liquid formulations. Other variations call for solid formulations. All such variations are intended to be within the scope and spirit of the invention.

Although some embodiments are shown to include certain features or steps, the applicant specifically contemplates that any feature or step disclosed herein may be used together or in combination with any other feature or step in any embodiment of the invention. It is also contemplated that any feature or step may be specifically excluded from any embodiment of the invention.

What is claimed is:

1. A method for endophytic colonization of a locus of a plant, comprising the steps of: inoculating the locus of the plant with *Clonostachys rosea*; and thereafter treating said locus with a chemical fungicide at least about 48 hours after said inoculating, wherein the biomass of said *Clonostachys rosea* is increased compared to treating the locus concurrently with said chemical fungicide.

2. The method of claim 1, wherein the inoculating comprises a liquid suspension comprised of *Clonostachys rosea* conidia in such quantity as to result in the colonization of the locus with mycelium wherein mycelial state is substantially unaffected by subsequent application of chemical fungicides.

3. The method of claim 1, wherein the inoculating occurs as a dust or wettable powder comprised of *Clonostachys rosea* conidia in such quantity as to result in the colonization of the locus with mycelium wherein mycelial state is substantially unaffected by subsequent application of chemical fungicides.

4. The method of claim 1, wherein the inoculating comprises applying said *Clonostachys rosea* to foliage, stems, flowers or fruit during a period when plants are growing in such quantity as to result in the colonization of at least part of the locus with mycelium.

5. The method of claim 1, wherein the inoculating comprises a suspension of a wettable powder that comprises the *Clonostachys rosea* and an adjuvant having a capability of increasing speed of the colonization of *Clonostachys rosea*, and subsequent colonization of the *Clonostachys rosea*, preventing ultra-violet inactivation of the *Clonostachys rosea*.

6. The method of claim 1, wherein the locus of the plant are seeds, and germination of said seeds is increased compared to treating the seeds concurrently with the chemical fungicide.

* * * * *